US012767761B2

(12) United States Patent
Kawamoto et al.

(10) Patent No.: US 12,767,761 B2
(45) Date of Patent: Oct. 20, 2026

(54) BISMALEIMIDE COMPOUND, COMPOSITION CONTAINING SAME, POLYBENZOXAZOLE, AND SEMICONDUCTOR DEVICE

(71) Applicant: Nippon Kayaku Kabushiki Kaisha, Tokyo (JP)

(72) Inventors: Naoki Kawamoto, Tokyo (JP); Firyon Ko, Tokyo (JP); Taihei Koumoto, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 888 days.

(21) Appl. No.: 18/107,286

(22) Filed: Feb. 8, 2023

(65) Prior Publication Data

US 2023/0250233 A1 Aug. 10, 2023

(30) Foreign Application Priority Data

Feb. 9, 2022 (JP) ................................ 2022-018705

(51) Int. Cl.

*C08G 73/22* (2006.01)
*C07D 207/452* (2006.01)
*G03F 7/038* (2006.01)
*H10W 74/47* (2026.01)

(52) U.S. Cl.

CPC ......... *C08G 73/22* (2013.01); *C07D 207/452* (2013.01); *G03F 7/038* (2013.01); *H10W 74/47* (2026.01)

(58) Field of Classification Search

CPC combination set(s) only.
See application file for complete search history.

(56) References Cited

U.S. PATENT DOCUMENTS

| | | | | |
|---|---|---|---|---|
| 4,371,685 | A | 2/1983 | Ahne et al. | |
| 6,080,522 | A | 6/2000 | Ito et al. | |
| 2002/0076535 | A1 | 6/2002 | Cooray | |
| 2003/0150557 | A1 * | 8/2003 | Sezi | C09J 5/06 156/330.9 |

(Continued)

FOREIGN PATENT DOCUMENTS

| | | | |
|---|---|---|---|
| JP | 2-37934 | B2 | 8/1990 |
| JP | 5-5995 | A | 1/1993 |

(Continued)

OTHER PUBLICATIONS

Notice of Allowance mailed Nov. 21, 2023 in co-pending U.S. Appl. No. 17/685,604.
Office Action mailed Jun. 20, 2023 in co-pending U.S. Appl. No. 17/685,604.
Office Action mailed Aug. 29, 2023 in co-pending U.S. Appl. No. 17/685,604.
Office Action mailed Dec. 31, 2025 in co-pending U.S. Appl. No. 18/107,285.
Final Rejection mailed Feb. 25, 2026 in co-pending U.S. Appl. No. 18/107,285.

(Continued)

*Primary Examiner* — Anca Eoff
(74) *Attorney, Agent, or Firm* — Nields, Lemack & Frame, LLC

(57) ABSTRACT

A bismaleimide compound represented by formula (1):

(1)

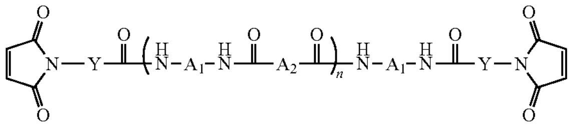

wherein $A_1$ represents a direct bond, a divalent linking group represented by formula (1-1), (1-2), or (1-3):

(1-1)

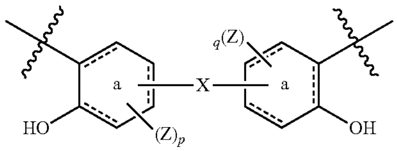

(1-2)

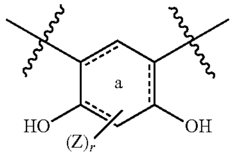

(1-3)

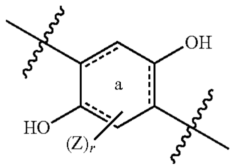

wherein ring a represents a benzene ring or a cyclohexane ring; X represents a direct bond or a divalent linking group; and Z represents a monovalent substituent; and $A_2$ represents a divalent linking group that is a residue of a saturated aliphatic dicarboxylic acid compound, a divalent linking group that is a residue of an aromatic dicarboxylic acid compound, or a divalent linking group other than this; and when $A_2$ is present singly, $A_2$ is a divalent linking group that is a residue of a saturated aliphatic dicarboxylic acid compound, and when a plurality of $A_2$ S is present, at least one of $A_2$s is a divalent linking group that is a residue of a saturated aliphatic dicarboxylic acid compound.

17 Claims, No Drawings

(56) References Cited

U.S. PATENT DOCUMENTS

| | | | |
|---|---|---|---|
| 2004/0063895 A1 | 4/2004 | Sezi et al. |
| 2010/0324163 A1 | 12/2010 | Shinjo |
| 2022/0298281 A1 | 9/2022 | Kawamoto et al. |
| 2023/0112804 A1 | 4/2023 | Ogasawara et al. |
| 2023/0305400 A1 | 9/2023 | Kawamoto et al. |

FOREIGN PATENT DOCUMENTS

| | | | |
|---|---|---|---|
| JP | 6-161102 | A | 6/1994 |
| JP | 6-289626 | A | 10/1994 |
| JP | 11-24271 | A | 1/1999 |
| JP | 11-199557 | A | 7/1999 |
| JP | 2001-106784 | A | 4/2001 |
| JP | 2001-266648 | A | 9/2001 |
| JP | 2002-138248 | A | 5/2002 |
| JP | 2004-68005 | A | 3/2004 |
| JP | 2004-118123 | A | 4/2004 |
| JP | 2008-266635 | A | 11/2008 |
| JP | 2012-68413 | A | 4/2012 |
| WO | 2018/181340 | A1 | 10/2018 |
| WO | 2021/123116 | A1 | 6/2021 |
| WO | 2021/187355 | A1 | 9/2021 |

OTHER PUBLICATIONS

Hai et al., Polymerization of diaspirin cross-linked hemoglobin (DCLHb) with water-soluble, nonimmunogenic polyamide cross-linking agents. Bioconjug Chem. Nov.-Dec. 1999;10(6):1013-20.

Kashiwada et al., Monodispersed Dimerization of Isoleuclne Zipper-Coiled Coil Trimer, Bulletin of the Chemical Society of Japan, vol. 80, Issue 7, Jul. 2007, pp. 1296-1301.

Reinecke et al., “Poly-Diels-Alder additions with disorboylamides as bisdienes and a dimaleoyiamide as bisdienophiie.” Macromol. Chem. Phys. 195, 2445-2455 (1994).

Japanese communication, with English translation, dated May 7, 2026 in co-pending Japanese patent application No. 2023-006910.

Japanese communication, with English translation, dated May 7, 2026 in corresponding Japanese patent application No. 2023-006911.

Notice of Allwance mailed May 27, 2026 in co-pending U.S. Appl. No. 18/107,285.

* cited by examiner

BISMALEIMIDE COMPOUND, COMPOSITION CONTAINING SAME, POLYBENZOXAZOLE, AND SEMICONDUCTOR DEVICE

This application claims priority under 35 U.S.C. § 119 of Japanese Patent Application No. 2022-018705 filed Feb. 9, 2022.

FILED OF THE INVENTION

Technical Filed

The present invention relates to a bismaleimide compound, a composition using the bismaleimide compound, a polybenzoxazole, and a semiconductor device. The bismaleimide compound of the present invention can be applied to a protective film, an interlayer insulating film, an insulating film of a rewiring layer, and the like for a semiconductor device.

BACKGROUND OF THE INVENTION

Background Art

Conventionally, a polyimide resin, a polybenzoxazole resin, and the like, which are excellent in heat resistance, mechanical properties, and the like, have been widely used for a surface protective film, an interlayer insulating film, and the like of a semiconductor device (see Patent Literature 1). When the polyimide resin or the polybenzoxazole resin is used as the surface protective film or the interlayer insulating film, a method for forming a through hole or the like by an etching method using a positive photoresist containing these resins is known. However, this method has a problem in which complicated steps such as coating and peeling of a photoresist are required. Therefore, for the purpose of streamlining working processes, a heat-resistant material to which photosensitivity is imparted has been studied (see Patent literature 2).

A thin film of the polyimide resin or the polybenzoxazole resin, which is excellent in heat resistance and mechanical properties, is generally obtained by thermally dehydrating and ring-closing a coated film of a precursor of the polyimide resin or the polybenzoxazole resin, and at that time, firing at a high temperature of about 350° C. is usually required. However, for example, next-generation memories such as a magnetoresistive random access memory (MRAM) and resins used for sealing these memories are weak against high temperatures. Therefore, a polyimide resin or a polybenzoxazole resin used for an interlayer insulating film of a fan-out wafer level package that forms a rewiring structure on a surface protective film or a sealing resin of such a device is required to be cured by firing at a low temperature of about 2 225° C. or less, and to obtain various properties comparable to those of a conventional material fired at a high temperature of about 350° C.

In addition, a polyimide resin that has been conventionally used needs to use a large amount of an organic solvent such as N-methyl-2-pyrrolidone in a step of developing the polyimide resin, and a cost becomes expensive. Therefore, in view of not only necessity of cost reduction but also safety and a recent increase in environmental problems, there is a demand for organic solvent removal. On the other hand, as with the photoresist, there have been proposed methods using various heat-resistant resin materials that can be developed (patterned) with a dilute aqueous alkali solution, such as a method in which a polyamic acid and a compound having an amino group, an amide group, a urethane group, or the like are mixed, and the mixture is heated after exposure in the presence of a photoinitiator (see Patent Literature 3), a method in which a quinone diazide is mixed with a salt of a polyamic acid and an amine compound having a phenolic hydroxyl group (see Patent Literature 4), and a method in which a polyamic acid and a base generator such as nifedipine are mixed (see Patent Literature 5).

Each of these methods uses a positive photosensitive composition based on a polyamic acid. Such a photosensitive composition exhibits relatively good developability, but has a small difference in solubility between an exposed portion and an unexposed portion, so that a pattern film loss is large, and photosensitivity is also insufficient. In addition, these compositions have a disadvantage that since a large amount of free carboxylic acid is present in a polymer backbone, the backbone is hydrolyzed over time by acidity of the polymer itself, and storage stability is extremely low.

Patent Literature 6 proposes a negative photosensitive material in which a hydroxyl group derived from an epoxy ring generated when a photosensitive group is introduced via an ester bond by allowing glycidyl methacrylate to act on a carboxy group of a polyamic acid is blocked with an intramolecular cyclic acid anhydride. However, since the photosensitive material of this document also has a large amount of free carboxylic acid in a polymer, there is a concern that storage stability is low due to an influence of hydrolysis of a backbone and a photosensitive side chain over time. In addition, such a photosensitive material has a further problem in which an imidization reaction unfavorably proceeds by heating at the time of introducing a photosensitive group, and a target polymer cannot be obtained.

Furthermore, a data communication amount of a communication terminal represented by a smartphone is continuously increasing, and a communication frequency is becoming higher in order to transmit a data amount in a short time. In order to increase the communication frequency, it is necessary to suppress a transmission loss, and a material having a low dielect constant and a low dielectric dissipation factor is required. However, it has been difficult to achieve both the properties as described above and dielectric properties.

CITATION LIST

Patent Literatures

Patent Literature 1: JP-A-11-199557
Patent Literature 2: JP-A-11-24271
Patent Literature 3: JP-A-06-289626
Patent Literature 4: JP-A-06-161102
Patent Literature 5: JP-A-05-5995
Patent Literature 6: JP-B-02-37934

BRIEF SUMMARY OF THE INVENTION

Technical Problem

An object of the present invention is to provide a novel bismaleimide compound.

A further object of the present invention is to provide a composition containing the novel compound, a polybenzoxazole, and a semiconductor device.

Another further object of the present invention is to provide a compound that is excellent in developability and from which a cured film (preferably a cured film excellent in thermal properties and electrical properties) can be obtained even by heat treatment at a low temperature of 225° C. or lower (or light irradiation and heat treatment at 225° C. or lower)

Solution to Problem

As a result of intensive studies, the present inventors have found that by using a polymer (heat-resistant resin) of a bismaleimide compound having a specific structure, a cured film containing a polybenzoxazole that is an intramolecular dehydrated ring-closed product of the polymer can be obtained even by heat treatment at a low temperature of 225° C. or lower (or light irradiation and heat treatment at 225° C. or lower).

That is, aspects and some preferred embodiments of the present invention are as follows.

[1].

A bismaleimide compound represented by the following formula (1):

(1)

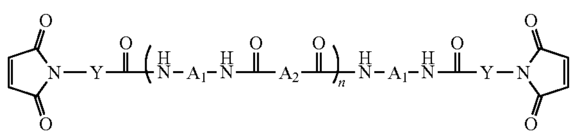

wherein, in formula (1), $A_1$s each independently represent a direct bond, a divalent linking group represented by the following formula (1-1), (1-2), or (1-3):

(1-1)

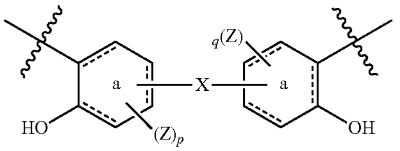

(1-2)

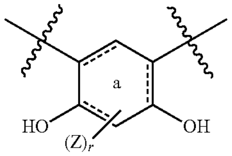

(1-3)

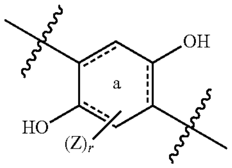

wherein, in formulas (1-1), (1-2), and (1-3), ring a represents a benzene ring or a cyclohexane ring; X represents a direct bond or a divalent linking group, and when a plurality of Xs is present in formula (1), the plurality of Xs may be the same as or different from each other; Z represents a monovalent substituent bonded to ring a, and when a plurality of Zs is present in formula (1), the plurality of Zs may be the same as or different from each other; p, q, and r are the number of monovalent substituents Z, p and q each independently represent an integer of 0 to 3, r represents an integer of 0 to 2, and when a plurality of ps is present in formula (1), the plurality of ps may be the same as or different from each other, when a plurality of qs is present in formula (1), the plurality of qs may be the same as or different from each other, and when a plurality of rs is present in formula (1), the plurality of rs may be the same as or different from each other;

or a divalent linking group other than formulas (1-1), (1-2), and (1-3) provided that at least one of the plurality of $A_1$s is a divalent linking group represented by formula (1-1), (1-2), or (1-3); $A_2$ represents a divalent linking group obtained by removing two carboxy groups from a saturated aliphatic dicarboxylic acid compound, a divalent linking group obtained by removing two carboxy groups from an aromatic dicarboxylic acid compound, or a divalent linking group other than a divalent linking group obtained by removing two carboxy groups from a saturated aliphatic dicarboxylic acid compound and a divalent linking group obtained by removing two carboxy groups from an aromatic dicarboxylic acid compound, and when a plurality of $A_2$s is present, the plurality of $A_2$s may be the same as or different from each other; when $A_2$ is present singly, $A_2$ is a divalent linking group obtained by removing two carboxy groups from a saturated aliphatic dicarboxylic acid compound, and when a plurality of $A_2$s is present, at least one of the plurality of $A_2$s is a divalent linking group obtained by removing two carboxy groups from a saturated aliphatic dicarboxylic acid compound; Y represents a divalent linking group, and a plurality of Ys may be the same as or different from each other; and n is an average value of the number of repeating units and is a real number in a range of 1 to 100.

[2].

The bismaleimide compound according to [1], wherein all of $A_1$s are a divalent linking group represented by formula (1-1), (1-2), or (1-3).

[3].

The bismaleimide compound according to [1] or [2], wherein at least one of $A_2$s is an alkylene group having 1 to 30 carbon atoms.

[4].

The bismaleimide compound according to any one of [1] to [3], wherein all of $A_2$s are an alkylene group having 1 to 30 carbon atoms.

[5].

The bismaleimide compound according to any one of [1] to [4], wherein $A_2$s are each independently a divalent linking group obtained by removing two carboxy groups from a dicarboxylic acid compound selected from the group consisting of phthalic acid, isophthalic acid, 1,4-benzenedicarboxylic acid, 4,4'-dicarboxydiphenyl ether, 4,4'-dicarboxydiphenyl sulfone, 4,4'-biphenyldicarboxylic acid, benzophenone-4,4'-dicarboxylic acid, and 4,4'-stilbenedicarboxylic acid.

[6].

The bismaleimide compound according to any one of [1] to [5], wherein Xs are each independently a direct bond or a divalent linking group represented by any one of the following formulas (a) to (f):

(a)

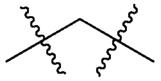

-continued (b)

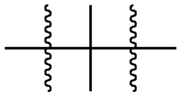

(c)

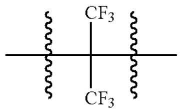

(d)

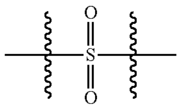

(e)

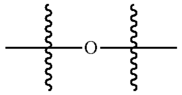

(f)

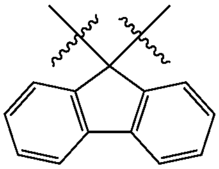

The bismaleimide compound according to any one of [1] to [6], wherein Ys are each independently an alkylene group having 1 to 11 carbon atoms, or a divalent group containing a divalent aromatic group obtained by removing two hydrogen atoms from an aromatic ring of an aromatic hydrocarbon compound and an alkylene group having 1 to 11 carbon atoms.

[8].

A composition comprising: the bismaleimide compound according to any one of [1] to [7]; and a photopolymerization initiator or a curing catalyst.

[9].

A composition comprising: the bismaleimide compound according to any one of [1] to [7]; and a compound capable of reacting with a maleimide group.

[10].

A polymer having 2 to 150 structural units represented by the following formula (2):

(2)

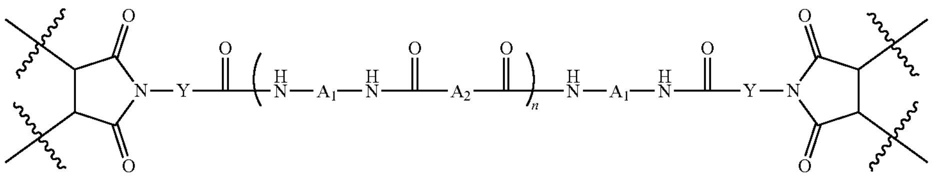

wherein $A_1$, $A_2$, Y, and n represent the same meaning as $A_1$, $A_2$, Y and n in formula (1), the polymer being a self-polymer of the bismaleimide compound according to any one of [1] to [7], a cured product of the composition according to [8], or a copolymer of the composition according to [9].

[11].

A polybenzoxazole that is an intramolecular dehydrated ring-closed product of the polymer according to [10].

[12].

A semiconductor device comprising a surface protective film, an interlayer insulating film, or an insulating film of a rewiring layer, wherein the film contains the polybenzoxazole according to [11].

[13].

A dry film resist comprising: two substrates; and the composition according to [8] sandwiched between the two substrates.

Advantageous Effects of Invention

The compound of the present invention can be developed with an alkaline aqueous solution, and by using a polymer formed from the compound, a cured film containing a polybenzoxazole can be obtained even by heat treatment at a low temperature of 225° C. or lower (or light irradiation and heat treatment at 225° C. or lower). The cured film according to a preferred embodiment of the present invention is excellent in thermal properties and electrical properties.

DETAILED DESCRIPTION OF THE INVENTION

Hereinafter, embodiments of the present invention will be described in detail, but the present invention is not limited to these embodiments.

A bismaleimide compound of the present invention (hereinafter, also simply referred to as "compound of the present invention") is represented by the following formula (1).

(1)

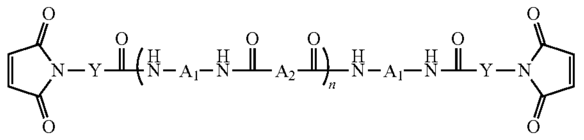

In formula (1), $A_1$s each independently represent a direct bond (it is an aspect in which two NHs specified on both sides of $A_1$ in formula (1) are directly bonded without interposing an atom, a divalent linking group, or the like, and the term "direct bond" is herein used in the same meaning), a divalent linking group represented by the following formula (1-1), (1-2), or (1-3), or a divalent linking group other than formulas (1-1), (1-2), and (1-3). It is noted that at least one of the plurality of $A_1$s is a divalent linking group represented by formula (1-1), (1-2), or (1-3).

(1-1)

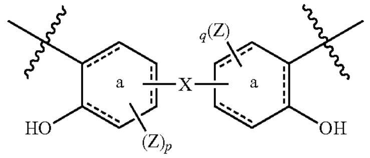

(1-2)

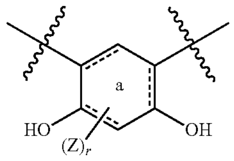

(1-3)

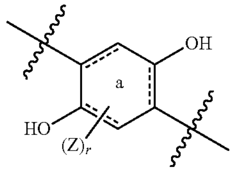

In formulas (1-1), (1-2), and (1-3), ring a represents a benzene ring or a cyclohexane ring. X represents a direct bond or a divalent linking group. Z represents a monovalent substituent of ring a, and when a plurality of Zs is present in formula (1), the plurality of Zs may be the same as or different from each other. p, q, and r are the number of substituents Z, p and q each independently represent an integer of 0 to 3, r represents an integer of 0 to 2, and when a plurality of ps is present in formula (1), the plurality of ps may be the same as or different from each other, when a plurality of qs is present in formula (1), the plurality of qs may be the same as or different from each other, and when a plurality of rs is present in formula (1), the plurality of rs may be the same as or different from each other.

When a plurality of divalent linking groups represented by formula (1-1), (1-2), or (1-3) is present in formula (1), all of a plurality of rings a present in formula (1) may be benzene rings, all of them may be cyclohexane rings, or both of benzene rings and cyclohexane rings may coexist. It is preferable that all of the plurality of rings a are benzene rings.

The divalent linking group represented by X in formula (1-1) is not particularly limited as long as it is a divalent linking group of a known diamine compound in which two 2-aminophenol compounds optionally having a substituent are bonded by a divalent linking group or a known diamine compound in which two 2-aminocyclohexanol compounds optionally having a substituent are bonded by a divalent linking group. As an example of the divalent linking group in the diamine compound, for example, a divalent linking group of 3,3"-diamino-4,4'-dihydroxydiphenyl ether is an oxygen atom, and a divalent linking group of 3,3'-diamino-4,4'-dihydroxydiphenylmethane is a methylene group.

The divalent linking group represented by X in formula (1-1) is preferably a divalent linking group represented by any one of the following formulas (a) to (f) from the viewpoint of solubility of a bismaleimide compound finally obtained and film physical properties of a cured product of a composition containing the bismaleimide compound (described below). Another preferred example of the divalent linking group represented by X includes —O—Ph—O—. A divalent linking group represented by any one of the following formulas (c) and (d) is more preferable.

(a)

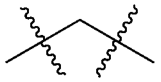

(b)

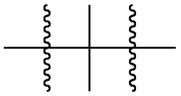

(c)

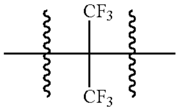

(d)

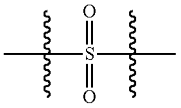

(e)

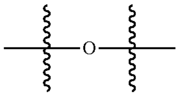

(f)

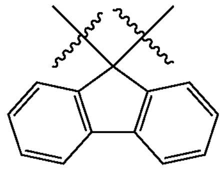

X in formula (1-1) is preferably a direct bond or a divalent linking group containing one or more selected from the group consisting of a carbon atom, a fluorine atom, a sulfur atom, and an oxygen atom. A direct bond or a divalent linking group represented by any one of the above formulas (a) to (f) is more preferable, and a direct bond or a divalent linking group represented by the above formula (c) or (d) is still more preferable.

The monovalent substituent represented by Z in formulas (1-1), (1-2), and (1-3) is not particularly limited, but is preferably a halogen atom, a hydroxyl group, a nitro group, a cyano group, an aliphatic group, an aromatic group, an acetyl group, a carboxy group, an ester group, an amide group, a trifluoromethyl group, an imide group, or a urea group. When a plurality of Zs is present, the respective Zs may be the same as or different from each other.

Specific examples of the halogen atom that is a preferred aspect of Z in formulas (1-1), (1-2), and (1-3) include a fluorine atom, a bromine atom, a chlorine atom, and an iodine atom. A fluorine atom is preferable.

The aliphatic group that is a preferred aspect of Z in formulas (1-1), (1-2), and (1-3) is a residue obtained by removing one hydrogen atom from a hydrocarbon compound having no aromaticity. The hydrocarbon compound is not limited to any of a linear form, a branched form, and a cyclic form, and may be a compound having a plurality of these forms.

Specific examples of the aliphatic group that is a preferred aspect of Z in formulas (1-1), (1-2), and (1-3) include alkyl groups having 1 to 6 carbon atoms such as a methyl group, an ethyl group, a propyl group, and a cyclohexane group, alkenyl groups having 1 to 6 carbon atoms such as propene, and alkynyl groups haying 1 to 6 carbon atoms such as propyne. A methyl group is preferable.

The aromatic group that is a preferred aspect of Z in formulas (1-1), (1-2), and (1-3) is a residue obtained by removing one hydrogen atom from an aromatic ring of an aromatic compound. The aromatic compound is not limited to any of an aromatic hydrocarbon compound, an aromatic heterocyclic compound, a heterocyclic condensed aromatic compound, and the like as long as it is a compound haying aromaticity.

Specific examples of the aromatic group that is a preferred aspect of Z in formulas (1-1), (1-2), and (1-3) include a phenyl group and a naphthyl group. A phenyl group is preferable.

Specific examples of the ester group that is a preferred aspect of Z in formulas (1-1), (1-2), and (1-3) include a metboxycarbonyl group, an ethoxycarbonyl group, an n-propoxycarbonyl group, a benzyloxycarbonyl group, and a phenoxycarbonyl group. A phenoxycarbonyl group is preferable.

Specific examples of the amide group that is a preferred aspect of Z in formulas (1-1), (1-2), and (1-3) include alkylamide groups such as $—CONH_2$, $—CONH(CH_3)$, and $—CONH(i\text{-}C_3H_7)$; and arylamide groups such as a benzamide group, a naphthamide group, a p-t-butylbenzamide group, an o-chlorobenzamide group, and $—CON(Ph)_2$. A benzamide group is preferable. In the present specification, Ph represents a phenyl group.

Z in formulas (1-1), (1-2), and (1-3) is more preferably an aliphatic group from the viewpoint of ease of intramolecular dehydration and ring closure of the polymer at a low temperature.

It is preferable that p, q, and r in formulas (1-1), (1-2), and (1-3) are each independently an integer of 0 or 1.

The divalent linking group other than formulas (1-1), (1-2), and (1-3) represented by $A_1$ in formula (1) is not particularly limited as long as it is a divalent linking group obtained by removing two amino groups from a diamine compound having no phenolic hydroxyl group (with the exception of hydrazine). Examples of the diamine compound that can be the divalent linking group include an aliphatic diamine having no phenolic, hydroxyl group and an aromatic diamine having no phenolic hydroxyl group. Preferred are aliphatic diamines including linear aliphatic diamines such as ethylenediamine, 1,3-propanediamine, and 1,4-butanediamine, aliphatic diamines having an alicyclic structure such as norbornanediamine and 1,3-bisaminomethylcyclohexane, and aliphatic diamines having a branched structure such as a dimer diamine. A dimer diamine is preferable from the viewpoint of solubility of a bismaleimide compound finally obtained and film physical properties of a cured film of a composition containing the bismaleimide compound.

The dimer diamine is obtained by substituting two carboxyl groups of a dimer acid, which is a dimer of an unsaturated fatty acid such as oleic acid, with primary amino groups (see, for example, JP-A-09-12712). Specific examples of commercially available products of the dimer diamine include PRIAMINE 1074 and PRIAMINE 1075 (both manufactured by Croda Japan K.K.), and Versamine 551 (manufactured by Cognis Japan Ltd.). These may be used alone, or two or more of these may be mixed for use. Non-limiting general formulas of the dimer diamine are shown below (in each formula, m+n is preferably 6 to 17, p+q is preferably 8 to 19, and a broken line part means a carbon-carbon single bond or a carbon-carbon double bond).

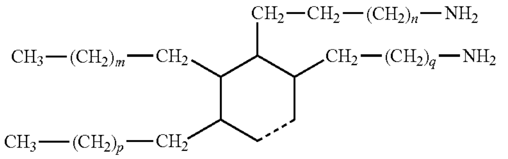

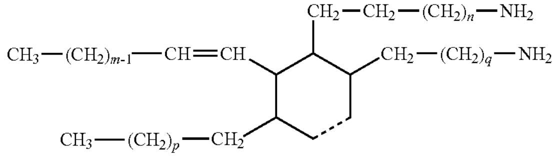

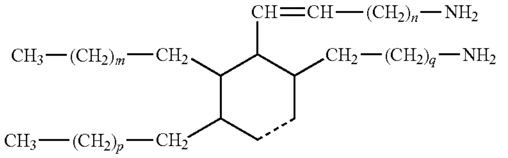

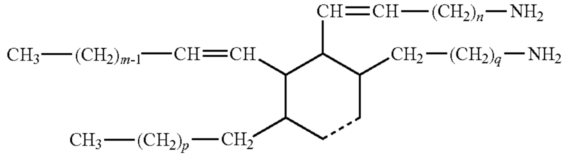

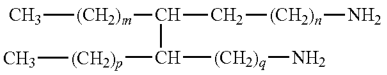

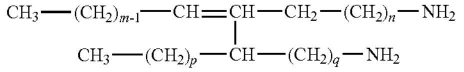

When a divalent linking group obtained by removing two amino groups from a diamine compound having no phenolic hydroxyl group or a direct bond is introduced into $A_1$ in formula (1), an introduction amount of a divalent linking group derived from a diamine compound having no phenolic hydroxyl group is preferably 30% or less of all $A_1$s from the viewpoint of solubility of a bismaleimide compound finally obtained and film physical properties of a cured film of a composition containing the bismaleimide compound. The phrase "30% or less of all $A_1$s" as used herein means that, for example, when the compound of the present invention has 10 $A_1$ units, the number (average) of direct bonds and divalent linking groups derived from a diamine compound having no phenolic hydroxyl group is 1 to 3. The introduction amounts of direct bonds and divalent linking groups derived from a diamine compound can be adjusted by a content (mol %) of hydrazine and a diamine compound having no phenolic hydroxyl group in a diamine component used in synthesizing the compound of the present invention.

As $A_1$ in formula (1), it is preferable that all of $A_1$s are a divalent linking group selected from the group consisting of formulas (1-1), (1-2), and (1-3), or at least one of $A_1$s is a divalent linking group obtained by removing two amino groups from an aliphatic diamine compound, and the rest of $A_1$s are a divalent linking group selected from the group consisting of formulas (1-1), (1-2), and (1-3). As $A_1$ in formula (1), it is more preferable that at least one of $A_1$s is a divalent linking group obtained by removing two amino groups from a dimer diamine, and the rest of $A_1$s are a divalent linking group of formula (1-1), (1-2), or (1-3).

In formula (1), $A_2$ represents a divalent linking group obtained by removing two carboxy groups from a saturated aliphatic dicarboxylic acid compound, a divalent linking group obtained by removing two carboxy groups from an aromatic dicarboxylic acid compound, or a divalent linking group other than a divalent linking group obtained by removing two carboxy groups from a saturated aliphatic dicarboxylic acid compound and a divalent linking group obtained by removing two carboxy groups from an aromatic dicarboxylic acid compound (hereinafter, simply referred to as "other divalent linking group"). When a plurality of $A_2$s is present, the plurality of $A_2$s may be the same as or different from each other. when $A_2$ is present singly, $A_2$ is a divalent linking group obtained by removing two carboxy groups from a saturated aliphatic dicarboxylic acid compound, and when a plurality of $A_2$s is present, at least one of the plurality of $A_2$s is a divalent linking group obtained by removing two carboxy groups from a saturated aliphatic dicarboxylic acid compound.

Examples of the saturated aliphatic dicarboxylic acid compound that can be the divalent linking group for $A_2$ include, but are not limited to, maionic acid, dimethylmalonic acid, ethylmalonic acid, isopropylmalonic acid, di-n-butylmalonic acid, succinic acid, tetrafluorosuccinic acid, methylsuccinic acid, 2,2-dimethylsuccinic acid, 2,3-dimethylsuccinic acid, glutaric acid, hexafluoroglutaric acid, 2-methylglutaric acid, 3-methylglutaric acid, 2,2-dimethylglutaric acid, 3,3-dimethylglutaric acid, 3-ethyl-3-mnethylglutaric acid, adipic acid, octafluoroadipic acid, 3-methyladipic acid, pimelic acid, 2,2,6,6-tetramethylpimelic acid, suberic acid, dodecafluorosuberic acid, azelaic acid, sebacic acid, hexafluorosebacic acid, 1,9-nonanedioic acid, dodecanedioic acid, tridecanedioic acid, tetradecanedioic acid, pentadecanedioic acid, hexadecanedioic acid, heptadecanedioic acid, octadecanedioic acid, nonadecanedioic acid, pentacosanedioic acid, hexacosanedioic acid, heptacosanedioic acid, octacosanedioic acid, nonacosanedioic acid, triacontanedioic acid, hentriacontanedioic acid, dotriacontanedioic acid, diglycolic acid, and the like. An aliphatic chain may partially contain a hetero atom such as an oxygen atom or a sulfur atom.

Among them, from the viewpoint of mechanical properties of a cured film, those in which the number of carbon atoms in a divalent saturated aliphatic chain obtained by removing two carboxy groups from a saturated aliphatic dicarboxylic acid compound is 4 or more are preferable. The number of carbon atoms is more preferably 4 or more and 20 or less, and still more preferably 4 or more and 10 or less.

When the number of carbon atoms in a saturated aliphatic chain is 4 or more, a cured film having sufficient mechanical properties can be obtained. When the number of carbon atoms in a saturated. aliphatic chain is 20 or less, compatibility between the compound and other components and photosensitive properties of a polybenzoxazole formed from a polymer of the compound can be kept good.

Examples of the aromatic dicarboxylic acid compound that can be the divalent linking group include, but are not limited to, phthalic acid, isophthalic acid, 1,4-benzenedicarboxylic acid, 4,4'-dicarboxydiphenyl ether, 4,4'-dicarboxydiphenyl sulfone, 4,4'-biphenyldicarboxylic acid, benzophenone-4,4'-dicarboxylic acid, 4,4'-stilbenedicarboxylic acid, and the like. From the viewpoint of film physical properties and solubility, a divalent linking group obtained by removing two carboxy groups from isophthalic acid and a divalent linking group obtained by removing two carboxy groups from 4,4'-dicarboxydiphenyl ether are preferable. By introducing a divalent linking group obtained by removing two carboxy groups from an aromatic dicarboxylic acid compound into $A_2$, film physical properties such as thermal properties and electrical properties of a cured film of a composition containing the bismaleimide compound represented by formula (1) can be improved. These compounds can be used alone or in combination of two or more.

The dicarboxylic acid compound that can be the other divalent linking group is not particularly limited as long as it is a dicarboxylic acid compound other than a saturated aliphatic dicarboxylic acid compound and an aromatic dicarboxylic acid compound, and examples thereof include an unsaturated aliphatic dicarboxylic acid compound. Examples of the unsaturated aliphatic dicarboxylic acid compound that can be the other divalent linking group include, but are not limited to, methylene succinic acid, allyl malonic acid, isopropylidene succinic acid, 2,4-hexadiene diacid, acetylenedicarboxylic acid, and the like.

In formula (1), Y represents a divalent linking group, and a plurality of Ys may be the same as or different from each other.

The divalent linking group represented by Y in formula (1) is not particularly limited, and may be a direct bond, but is preferably an alkylene group having 1 to 11 carbon atoms, or a divalent group containing a divalent aromatic group obtained by removing two hydrogen atoms from an aromatic ring of a hydrocarbon compound and an alkylene group having 1 to 11 carbon atoms. The alkylene group is not limited to a linear alkylene group, and may be a branched alkylene group or a cyclic alkylene group.

The divalent group containing a divalent aromatic group obtained by removing two hydrogen atoms from an aromatic ring of a hydrocarbon compound and an alkylene group having 1 to 11 carbon atoms as used herein may be a divalent linking group in which one alkylene group and one aromatic group are bonded, a divalent linking group in which one alkylene group and a plurality of aromatic groups are bonded, a divalent linking group in which two alkylene groups and one aromatic group are bonded, or a divalent linking group in which a plurality of alkylene groups and a plurality of aromatic groups are bonded as long as the total number of carbon atoms in a backbone of an alkylene group moiety is 11 or less.

The divalent linking group represented by in formula (1) is more preferably an alkylene group having 1 to 11 carbon atoms from the viewpoint of solubility of a bismaleimide compound finally obtained and film physical properties of a cured film containing a polybenzoxazole obtained from a polymer of the bismaleimide compound. An alkylene group having 2 to 8 carbon atoms is further preferable, a linear alkylene group having 2 to 8 carbon atoms or an alkylene group represented by the following formula (g) is particularly preferable, and a linear alkylene group having 5 carbon atoms is most preferable.

(g)

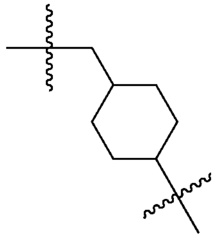

A weight average molecular weight of the bismaleimide compound represented by formula (1) is preferably 1,000 to 200,000, and more preferably 1,000 to 100,000. When the weight average molecular weight is 1,000 or more, a strength and film physical properties of a cured film containing a polybenzoxazole obtained from a polymer of the bismaleimide compound of the present invention can be improved, and furthermore, when a composition containing the bismaleimide compound is film-formed by spin coating, a desired film thickness can be easily obtained. When the weight average molecular weight is 200,000 or less, solubility of the composition in an alkaline developer and resolution of the composition at the time of light irradiation can be highly maintained. Here, the weight average molecular weight is a value obtained by measuring by gel permeation chromatography and converting from a standard polystyrene calibration curve.

A method for producing the compound of the present invention is not particularly limited, but generally used is a method in which a diamine compound including a diaminodiphenol compound or a cyclohexane ring compound obtained by hydrogenating a benzene ring of a diaminodiphenol compound (hereinafter, referred to as a diaminodiphenol compound or a hydrogenated product thereof) and a dihalide derivative of a dicarboxylic acid compound including a saturated aliphatic dicarboxylic acid compound as an essential component and an aromatic dicarboxylic acid compound or another dicarboxylic acid compound (for example, an unsaturated aliphatic dicarboxylic acid compound) as an optional component are subjected to a dehydrochlorination reaction with an excess mole of the diamine compound (preferably, the diamine compound is used in an amount of 1.01 mol or more based on 1 mol of the dihalide derivative of a dicarboxylic acid compound) to obtain a dehydrochlorination reaction product; thereafter, a halide derivative of a maleimidocarboxylic acid is reacted with amino groups at both terminals of the dehydrochlorination reaction product obtained above. Alternatively, in this general production method, the diaminodiphenol compound can be replaced with a diaminocatechol compound (a raw material for production corresponding to the bismaleimide compound of formula (1) in which $A_1$ is formula (1-2) or (1-3)) (the same applies to the following description of the production method). The halide derivative of a maleimidocarboxylic acid can be used alone or in combination of two or more.

When diamines having no phenolic hydroxyl group are used in combination for the reaction, a procedure of the reaction is not particularly limited as long as the total number of moles of the diamine compound used in the reaction is more than the number of moles of the dihalide derivative of a dicarboxylic acid compound. For example, both of the diaminodiphenol compound or a hydrogenated product thereof and the diamines having no phenolic hydroxyl group may be mixed in advance and reacted with the dihalide derivative of a dicarboxylic acid compound, or only one of the diaminodiphenol compound or a hydrogenated product thereof and the diamines having no phenolic hydroxyl group may be first reacted with the dihalide derivative of a dicarboxylic acid compound, and then the other may he added and reacted.

As the dihalide derivative of a dicarboxylic acid compound, a dichloride derivative is preferable. Examples of a halogenating agent used in conversion into a dichloride derivative include thionyl chloride, oxalyl chloride, phosphoryl chloride, and phosphorus chloride, which are used in an ordinary acid chlorination reaction. As the dichloride derivative of a dicarboxylic acid compound, a commercially available product may be used.

As the halide derivative of a maleimidocarboxylic acid to be reacted with amino groups at both terminals of the dehydrochlorination reaction product, a halide derivative synthesized by a known method may be used, or a commercially available product may be used. When a synthesized halide derivative is used, a maleimidocarboxylic acid may be halogenated using a halogenating agent.

Examples of the maleimidocarboxylic acid that can be the halide derivative of a maleimidocarboxylic acid include the following compounds Nos. 1 to 4. The halide derivative of a maleimidocarboxylic acid obtained from these maleimidocarboxylic acids can be used alone or in combination of two or more.

No.1

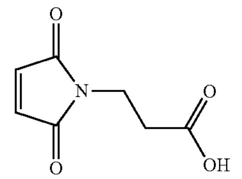

No. 2

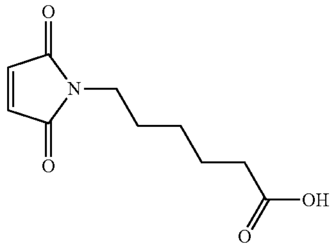

No. 3

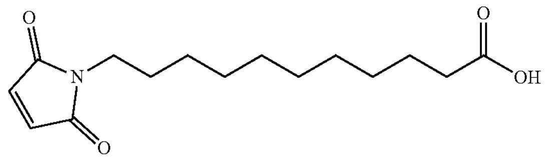

No. 4

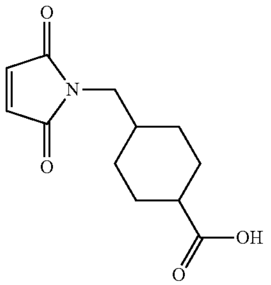

Examples of the diaminodiphenol compound or a hydrogenated product thereof used in production of the compound of the present invention include the following compounds Nos. 5 to 12 and cyclohexane ring compounds obtained by hydrogenating benzene rings in compounds Nos. 5 to 12. These diaminodiphenol compounds or hydrogenated products thereof can be used alone or in combination of two or more.

No. 5

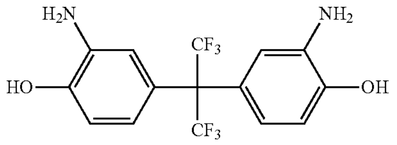

-continued

No. 6

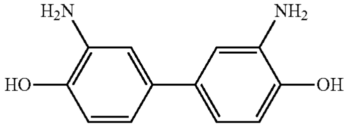

No. 7

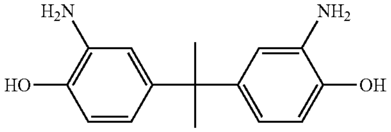

No. 8

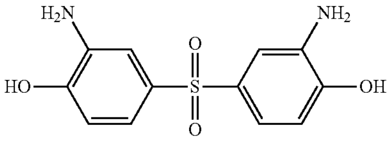

No. 9

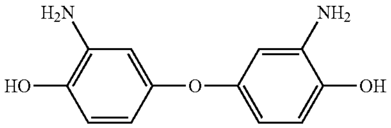

No. 10

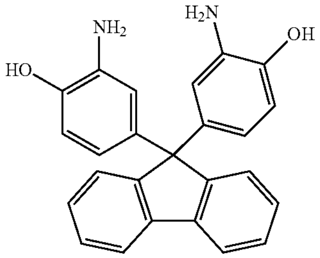

No. 11

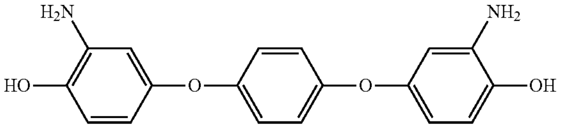

No. 12

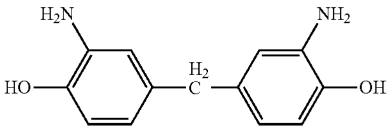

The reaction between the dihalide derivative of a dicarboxylic acid compound and the diamine compound or a hydrogenated product thereof is desirably performed in an organic solvent in the presence of a dehalogenating agent. As the dehalogenating agent, usually, an organic base such as pyridine, 2-methylpyridine, or triethylamine can be used. As the organic solvent, sulfolane, N,N-dimethylacetamide, N-methyl-2-pyrrolidone, N,N-dimethylformamide, or the like can be used. A concentration of a reaction component group with respect to an entire reaction system including the solvent is not particularly limited, but is preferably 20 to 80% by mass, and more preferably 40 to 60% by mass.

As a specific synthesis procedure, a diamine compound is dissolved in an organic solvent, and a dihalide derivative of a dicarboxylic acid compound is added thereto. A temperature at which the dihalide derivative of a dicarboxylic acid compound is added is preferably −20 to 35° C., and more preferably −10 to 30° C. A temperature at which the diamine compound is reacted with the dihalide derivative of a dicarboxylic acid compound is preferably 0 to 80° C., and more preferably 10 to 40° C. A reaction time is preferably 30 minutes to 24 hours, and more preferably 1 to 5 hours. Subsequently, a halide derivative of a maleimidocarboxylic acid is added to the reaction system. A temperature at which the halide derivative of a maleimidocarboxylic acid is added is preferably −20 to 20° C., and more preferably −10 to 10° C. A subsequent reaction temperature is preferably 0 to 30° C., and more preferably 0 to 10° C. A reaction time is preferably 10 minutes to 3 hours, and more preferably 30 minutes to 2 hours. After completion of the reaction, water is added to the obtained reaction solution, whereby the bismaleimide compound of the present invention can be obtained.

Impurities can be removed by using an acidic aqueous solution, an alkaline aqueous solution, or a neutral aqueous solution, and further an organic solvent or the like for the compound obtained by the above procedure.

The above description relates to a method for producing the compound of the present invention using a diamine compound including a diaminodiphenol compound or a hydrogenated product thereof, a dihalide derivative of a dicarboxylic acid compound, and a halide derivative of a maleimidocarboxylic acid. Alternatively, the compound of the present invention may be produced by a known dehydration condensation reaction using a diaminodiphenol compound or a hydrogenated product thereof, a dicarboxylic acid compound, and a maleimidocarboxylic acid.

Next, the polymer of the present invention will be described.

The compound represented by formula (1) of the present invention is a polymer (self-polymer) obtained by self-polymerization of the compound represented by formula (1) via maleimide groups at both terminals, or a polymer (copolymer) obtained by copolymerization of the compound represented by formula (1) and a compound capable of reacting with a maleimide group, and can be the polymer of the present invention having a structural unit represented by the following formula (2). That is, the self-polymer has a structure in which a plurality of unit structures represented by the following formula (2) are directly bonded. The copolymer has a structure in which a plurality of unit structures represented by the following formula (2) are bonded via a linking group other than formula (2). The number of unit structures represented by formula (2) in the polymer of the present invention is not particularly limited, but is preferably 2 to 150.

$A_1$, $A_2$, Y, and n in the unit structure represented by formula (2) represent the same meaning as $A_1$, $A_2$, Y, and n in formula (1), and preferred ones are also the same as those in formula (1).

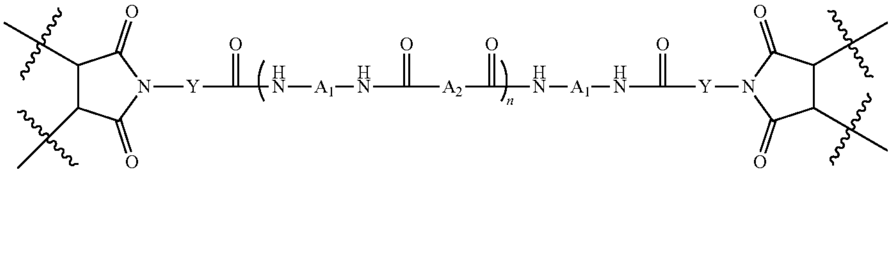

(2)

The self-polymer can be obtained only by heating the compound represented by formula (1) alone under various conditions that are usually used when maleimide groups are self-polymerized, for example, at 40 to 150° C. for about 30 to 300 minutes. Heating may be performed under relatively mild conditions, for example, at 50 to 70° C. for about 60 to 180 minutes to obtain a mixture with a self-polymer having the structural unit represented by formula (2) containing the compound represented by formula (1) as a main component, or heating may be performed under relatively severe conditions, for example, at 80° C. to 150° C. for about 30 to 120 minutes to obtain a mixture with the compound represented by formula (1) containing a self-polymer having the structural unit represented by formula (2) as a main component. Since a ratio between the compound represented by formula (1) and the self-polymer in the mixture produced affects handling and the like when the mixture is subjected to a subsequent step, reaction conditions may be optimized so that the ratio between the compound and the self- polymer falls within a desired range in consideration of handling and the like.

Even in a mixture containing the compound represented by formula (1) as a main component, a self-polymerization reaction also occurs by heating during a ring-closing reaction for benzimidazolization, and thus, there is no undesirable influence on various physical properties of finally obtained polybenzimidazole (described below).

In addition, by forming a composition in which a photopolymenzation initiator or a curing catalyst is used in combination with the compound represented by formula (1) (described below), a self-polymer can also be formed by light irradiation or heating at a temperature lower than that in the case of the compound alone (the case of not using a photopolymerization initiator or a curing catalyst in combination).

The copolymer is obtained by a copolymerization reaction of a composition in which a compound capable of reacting with a maleimide group is used in combination with the compound represented by formula (1) (described below).

Next, a composition of the present invention will be described.

A composition of a first aspect of the present invention contains at least one of the hismaleimide compounds of the present invention represented by formula (1), and at least one of photopolymerization initiators or at least one of curing catalysts.

The photopolymerization initiator used in the composition of the first aspect of the present invention is not particularly limited as long as it is a conventionally known photopolymerization initiator used for photocuring a compound having an unsaturated double bond group. Specific examples of the photopolymerization initiator include acetophenone, 2,2-dimethoxyacetophenone, p-dimethylaminoacetophenone, Michler's ketone, benzyl, benzoin, benzoin methyl ether, benzoin ethyl ether, -benzoin isopropyl ether, benzoin n-propyl ether, benzoin isobutyl ether, benzoin n-butyl ether, benzyl dimethyl ketal, thioxanthene, 2-chlorothioxanthone, 2-methylthioxanthone, 2,2-dimethoxy-1,2-diphenylethan-1-one, 1-hydroxy-cyclohexyl-phenyl-ketone, 2-hydroxy-2-methyl-1-phenyl-propan-1-one, 1-[4-(2-hydroxyethoxy)-phenyl]-2-hydroxy -2-methyl-1-propan-1-one, 2-hydroxy-1-{4-[4-(2-hydroxy-2-methyl-propionyl)-benzyl]phenyl}-2-methyl-propan-1-one, 2-methyl-1-[4-(methylthio)phenyl]-2-morpholinopropan-1-one, 2-benzyl-2-dimethylamino-1-(4-morpholinophenyl)-1-butanone, 2,4,6-trimethylbenzoyl-diphenyl-phosphine oxide, bis(2,4,6-trimethylbenzoyl)-phenylphosphine oxide, 1-[4-(phenylthio)phenyl]-1,2-octanedione=2-(O-benzoyloxime), ethanone, 1-[9-ethyl-6-(2-methylbenzoyl)-9H-carbazol-3-yl]-, 1-(O-acetyloxime), and 2,4-diethylthioxanthone. These photopolymerization initiators may be used alone or in combination of two or more.

Among them, from the viewpoint that a fine pattern can be formed by a reduction projection exposure machine (stepper, light source wavelength: 365 nm, 436 nm) that is typically used in a step of manufacturing a semiconductor protective film or the like, it is preferable to use a photopolymerization initiator that efficiently generates radicals at an exposure wavelength of 310 to 436 nm (more preferably 365 nm). Preferable examples of the photopolymerization initiator include 1-[4-(phenylthio)phenyl]-1,2-octanedione=2-(O-benzoyloxime) ("IRGACURE OXE-01" manufactured by BASF Japan Ltd.), ethanone, 1-[9-ethyl-6-(2-methylbenzoyl)-9H-carbazol-3-yl]-, 1-(O-acetyloxime) ("IRGACURE OXE-02" manufactured by BASF Japan Ltd.), 2,4-diethylthioxanthone ("DETX-S" manufactured by Nippon Kayaku Co., Ltd.), and 2-methyl-1-[4-(methylthio) phenyl]-2-morpholinopropan-1-one ("Omnirad 907" manufactured by IGM Resins B.V.).

A use amount of the photopolymerization initiator is preferably 0.1 to 20 parts by mass, and more preferably 1 to 5 parts by mass based on 100 parts by mass of the compound represented by formula (1) (when the photopolymerization initiator is used).

A sensitizer may be used in combination with a photopolymerization initiator in the composition of the first aspect containing the photopolymerization initiator. The sensitizer that can be used in combination is not particularly limited as long as it is a conventionally known sensitizer, and examples thereof include 4,4'-bis(diethylamino)benzophenone.

A use amount of the sensitizer is preferably 2 parts by mass or less, and more preferably 0.05 to 0.5 parts by mass based on 100 parts by mass of the compound represented by formula (1) (when the sensitizer is used). By using the sensitizer in combination, sensitivity to light during self-polymerization can be enhanced.

The curing catalyst used in the composition of the first aspect of the present invention is not particularly limited as long as it can promote self-polymerization of maleimide groups at both terminals of the compound represented by formula (1) of the present invention by heating, and those conventionally used can be appropriately adopted. Specific examples of the curing catalyst include imidazoles such as 2-methylimidazole, 2-ethylimidazole, 2-phenylimidazole, 2-ethyl-4-methylimidazole, 2-undecylimidazole, and 1-cyanoethyl-2-ethyl-4-methylimidazole; amines such as triethylamine, triethylenediamine, 2-(dimethylantinomethyl)phenol, 1,8-diaza-bicyclo(5,4,0)uldecene-7, tris (dimethylaminomethyl)phenol, and benzyldimethylamine; phosphines such as triphenylphosphine, tributylphosphine, and trioctylphosphine; organic metal salts such as tin octylate, zinc octylate, dibutyltin dimaleate, zinc naphthenate, cobalt naphthenate, and tin oleate; metal chlorides such as zinc chloride, aluminum chloride, and tin chloride; organic peroxides such as di-tert-butyl peroxide and dicumyl peroxide; azo compounds such as azobisisobutyronitrile and azobisdimethylvaleronitrile; mineral acids such as hydrochloric acid, sulfuric acid, and phosphoric acid; Lewis acids such as boron trifluoride; and salts such as sodium carbonate and lithium chloride.

A use amount of the curing catalyst is preferably 10 parts by mass or less, and more preferably 1 to 5 parts by mass based on 100 parts by mass of the compound represented by formula (1) (when the curing catalyst is used).

A composition of a second aspect of the present invention contains at least one of the bismaleimide compounds of the present invention represented by formula (1) and at least one of compounds capable of reacting with a maleimide group.

Examples of the compound capable of reacting with a maleimide group used in the composition of the second aspect of the present invention include a compound having a plurality of unsaturated double bonds such as an acrylic group, a methacrylic group, an allyl group, and a styryl group, and a compound having a functional group (or structure) capable of crosslinking reaction with a maleimide group such as an amino group, a cyanate group, a phenolic hydroxyl group, and an alcoholic hydroxyl group. In addition, a maleimide compound such as a bismaleimide compound other than the bismaleimide compound of the present invention may be used as a compound capable of reacting with a maleimide group.

The composition of the second aspect can be a copolymer only by heating under various conditions that are usually used when maleimide groups are self-polymerized. It is a preferred aspect that copolymerization is performed by light irradiation using a compound capable of reacting with a maleimide group in combination since sensitivity to light can be enhanced. In this case, a polyfunctional acrylate is more preferable from the viewpoint of facilitating a crosslinking reaction by photopolymerization.

Specific examples of the compound having a plurality of acrylic groups include hydrogenated dicyclopentadienyl diacrylate, dicyclopentenyl acrylate, dicyclopentenyloxyethyl acrylate, 1,3-butanediol diacrylate, 1,4-butanediol diacrylate, 1,6-hexanediol diacrylate, diethylene glycol diacrylate, neopentyl glycol diacrylate, polyethylene glycol 200 diacrylate, polyethylene glycol 400 diacrylate, polyethylene glycol 600 diacrylate, diethylene glycol diacrylate, neopentyl glycol diacrylate, hydroxypivalic acid ester neopentyl glycol diacrylate, triethylene glycol diacrylate, bis(acryloxyethoxy)bisphenol A, bis(acryloxyethoxy)tetrabromobisphenol A, tripropylene glycol diacrylate, trimethylolpropane triacrylate, pentaelythritol triacrylate, pentaerythritol tetraacrylate, dipentaerythritol hexaacrylate, and dipentaelythritol monohydroxypentaacrylate.

Specific examples of the compound having a plurality of methacrylic groups include a compound in which an acrylic group in the above compound having a plurality of acrylic groups is replaced with a methacrylic group.

Specific examples of the compound having a plurality of allyl groups include diallyl adipate, diallyl fumarate, diallyl hexahydrophthalate, pentaerythritol tetraallyl ether, glycerol diallyl ether, and triallyl citrate.

Specific examples of the compound having a plurality of styryl groups include bis(vinylphenyl)methane, bis(vinylphenyl)ethane, and bis(vinylphenyl)hexane.

A ratio between the compound represented by formula (1) used in a copolymerization reaction and the compound capable of reacting with a maleimide group is not particularly limited, but can be appropriately adjusted by a molecular weight of the compound capable of reacting with a maleimide group, the number of polymerizable functional groups, and the like. For example, an amount of the compound capable of reacting with a maleimide group is preferably 0.01 to 10 mol, and more preferably 0.1 to 1 mol, based on 1 mol of the compound represented by formula (1).

The copolymerization reaction may be performed under various conditions of the self-polymerization described above. The copolymerization reaction may be performed using a photo-polymerization initiator, a sensitizer, and a curing catalyst in combination. Usage of these substances is the same as described in the section of self-polymerization.

In the composition of the present invention, in addition to hie bismaleimide compound represented by formula (1), which is an essential component, and an optional photopolyrnerization initiator and/or curing catalyst, or a compound capable of reacting with a maleimide group, other components may be used in combination.

Examples of the other components that can be combinationaly used in the composition of the present invention include various additives such as an organic solvent, an adhesion enhancer such as a coupling agent, a thermoplastic resin, a colorant, a thickener, a thermal polymerization inhibitor, an antifoaming agent, and a leveling agent.

The organic solvent is not particularly limited, and examples thereof include γ-butyrolactone, ethyl lactate, propylene glycol monomethyl ether acetate, benzyl acetate, n-butyl acetate, ethoxyethyl propionate, 3-methylmethoxypropionate, N-methyl-2-pyrrolidone, N-ethyl-2-pyrrolidone, N,N-dimethylformamide, N,N-dimethylacetamide, dimethyl sulfoxide, hexamethylphosphorylamide, tetramethylene sulfone, cyclohexanone, cyclopentanone, diethyl ketone, diisobutyl ketone, and methyl amyl ketone. These organic solvents can be used alone or in combination of two or more. Use of organic solvents in combination is a preferred aspect in that handling of the composition is improved.

A content of the organic solvent in the composition of the present invention is not particularly limited, but the content of the solvent in the composition (when the organic solvent is used) is usually 95% by mass or less, and preferably 20 to 90% by mass.

The coupling agent as the adhesion enhancer is not particularly limited, but may typically be a silane coupling agent. The silane coupling agent is not particularly limited, and examples thereof include 3-chloropropyltrimethoxysilane, vinyltrichlorosilane, vinyltriethoxysilane, vinyltrimethoxysilane, vinyltris(2-methoxyethoxy)silane, 3-methacryloxypropyltrimethoxysilane, 2-(3,4-epoxycyclohexyl)ethyltrimethoxysilane, 3-glycidoxypropyltrimethoxysilane, 3-mercaptopropyltrimethoxysilane, 3-aminopropyltriethoxysilane, N-2-(aminoethyl)-3-aminopropyltrimethoxysilane, and 3-ureidopropyltriethoxysilane. These can be used alone or in combination of two or more.

Since the silane coupling agent is unreactive with the compound of the present invention and the like (compound, self-polymer, polybenzoxazole), components other than the component acting at a substrate interface may be present as a residual component after curing. Therefore, when the silane coupling agent as the adhesion enhancer is used in a large amount, there is a possibility that the silane coupling agent has an undesirable influence such as deterioration of physical properties. Depending on a type of a substrate, from the viewpoint of exerting an effect even in a small amount, it is appropriate to use the silane coupling agent within a range in which an undesirable influence is not exerted. A use ratio of the silane coupling agent is preferably usually 15% by mass or less, and more than 0% by mass and 5% by mass or less based on a total mass of the composition (when the silane coupling agent is used), but an upper limit of the use ratio can vary depending on the type of the substrate.

Examples of the thermoplastic resin include polyethersulfone, polystyrene, and polycarbonate.

Examples of the colorant include phthalocyanine blue, phthalocyanine green, iodine green, crystal violet, titanium oxide, carbon black, and naphthalene black.

Examples of the thickener include orbene, bentone, and montmorillonite.

Examples of the thermal polymerization inhibitor include hydroquinone and 2,6-di-tert-butyl-p-methylphenol.

Examples of the antifoaming agent include silicone-based, fluorine-based, and polymer-based antifoaming agents.

Each use amount of these additives is, for example, preferably 30% by mass or less in the composition of the present invention (when these additives are used) as a rough indication, but can be appropriately increased or decreased according to a purpose of use.

In the composition of the present invention, for example, an inorganic filler such as barium sulfate, barium titanate, silicon oxide, amorphous silica, talc, clay, magnesium carbonate, calcium carbonate, aluminum oxide, aluminum hydroxide, or mica powder may be used in combination. A blending ratio of the inorganic filler is preferably 60% by mass or less in the composition of the present invention (when the inorganic filler is used).

The composition of the present invention may contain a thermal acid generator (thermal latent acid generator) and a thermal base generator (thermal latent base generator). Use of the thermal acid generator or the thermal base generator is preferable because it efficiently works as a catalyst when the phenolic hydroxyl group-containing polyamide structure (nonphenolic hydroxyl group-containing polyamide structure when a benzene ring is hydrogenated to form a cyclohexane ring) of formula (2), which is a polybenzoxazole precursor, is cyclized by causing an intramolecular dehydration ring-closing reaction. In particular, a temperature of an intramolecular dehydration ring-closing reaction can be lowered by an acid generated from the thermal acid generator, and a cured film obtained at that time has performance comparable to that of a film cured at a high temperature.

The acid generated from the above thermal acid generator is preferably a strong acid. As such a strong acid, specifically, arylsulfonic acids such as p-toluenesulfonic acid and benzenesulfonic acid, and alkylsulfonic acids such as camphorsulfonic acid, trifluoromethylsulfonic acid, and nonafluorobutanesulfonic acid are preferable. These acids efficiently work as a catalyst when the phenolic hydroxyl group-containing polyamide structure (nonphenolic hydroxyl group-containing polyimide structure when a benzene ring is hydrogenated to form a cyclohexane ring) of formula (2), which is a polybenzoxazole precursor, is cyclized by causing an intramolecular dehydration ring-closing reaction.

The compound of the present invention and a composition containing the compound can also be used in a form of a dry film resist. That is, the compound and the composition of the present invention can be coated onto a base film using a roll coater, a die coater, a knife coater, a bar coater, a gravure coater, or the like, and then dried in a drying furnace set at 45 to 140° C. to remove a predetermined amount of solvent, or a cover film or the like can be laminated as necessary, thereby forming a dry film resist. At this time, a thickness of the resist on the base film is controlled within the range of from 2 to 200 μm. The compound and the composition of the present invention used for forming a dry film resist may be any of those described above as long as they contain the compound, but the composition of the first aspect described above is preferable. As the base film and the cover film, for example, films of polyester, polypropylene, polyethylene, TAC, polyimide, and the like are used. As these films, a film treated with a silicone-based release treatment agent or a non-silicone-based release treatment agent may be used as necessary. When supplied as a dry film resist, steps of coating on a support and drying can be omitted, and the composition of the present invention can be used more easily.

The polybenzoxazole of the present invention is an intramolecular dehydrated ring-closed product of the polymer (self-polymer and copolymer) of the present invention described above.

In the entire specification and appended claims, not only when ring a is a benzene ring but also when ring a is a cyclohexane ring formed by hydrogenation of a benzene ring, intramolecular dehydrated ring-closed products of polymers having the unit structure represented by formula (2) are collectively referred to as "polybenzoxazole" for convenience.

Various conditions for intramolecular dehydration ring-closing of the polymer of the present invention are not particularly limited as long as they are conditions that are usually used when a polybenzoxazole precursor is converted into a polybenzoxazole by an intramolecular dehydration ring-closing reaction. The intramolecular dehydration ring-closing reaction can be performed using, for example, a hot plate, an oven, or a temperature-raising type oven in which a temperature program can be set. The intramolecular dehydration ring-closing reaction may be performed in air or under an inert gas atmosphere such as nitrogen or argon.

The intramolecular dehydration ring-closing reaction of the polymer of the present invention can be advantageously performed at a low temperature of 225° C. or lower. A temperature of the intramolecular dehydration ring-closing reaction may be preferably lower than 225° C., and more preferably 215° C. or lower.

The cured film containing the polybenzoxazole of the present invention can be used for electronic components such as semiconductor devices and multilayer wiring boards, and organic EL display devices, Specifically, this cured film can be suitably used for applications such as a passivation film of a semiconductor, a surface protective film and an interlayer insulating film of a semiconductor device, an interlayer insulating film of a multilayer wiring for high-density mounting, an insulating film of a rewiring layer, an interlayer insulating film of an electronic component such as an inductor or an SAW filter, and an insulating film or a flat layer of an organic electroluminescent device, but is not limited thereto, and can have various structures.

EXAMPLES

Hereinafter, the present invention will be described more specifically with reference to Examples, but the present invention is not limited. to these Examples. Note that "part" and "%" in Examples are on a mass basis.

In Examples and Comparative Examples described below, a weight average molecular weight of a synthesized polymer was determined in terms of standard polystyrene using gel permeation chromatography (GPC, with the use of an apparatus manufactured by Tosoh Corporation, and a column manufactured by Tosoh Corporation).

Example 1

Synthesis of Bismaleimide Compound of the Present Invention 500 parts of N-methylpyrrolidone was charged into a 2-liter flask equipped with a stirrer and a thermometer, and 80.6 parts of 2,2'-bis(3-amino-4-hydroxyphenyl)hexafluoropropane and 52.3 parts of 2-methylpyridine were added and stirred and dissolved, and 47.8 parts of sebacic acid dichloride was added dropwise over 15 minutes while the solution was maintained at 30° C. or less, then stirring was continued at 30° C. for 3 hours. While the solution obtained above was maintained at 10° C. or lower, 11.0 parts of 6-maleimidohexanoic acid chloride was added dropwise over 10 minutes, and then stirring was continued for 1 hour. 1 L of water was added to the solution obtained above, and the precipitate was collected and washed three times with pure water, and then dried in an oven at 60° C. for 2 days to obtain a bismaleimide compound (AP-1) of the present invention. A weight average molecular weight (Mw) of the compound (AP-1) was 12,300.

Example 2

Synthesis of Bismaleimide Compound of the Present Invention 400 parts of N-methylpyrrolidone was charged into a 2-liter flask equipped with a stirrer and a thermometer, and 73.3 parts of 2,2'-bis(3-amino-4-hydroxyphenyl)hexafluaropropane and 66.4 parts of 2-methylpyridine were added and stirred and dissolved, and 23.9 parts of sebacic acid dichloride was added dropwise over 15 minutes while the solution was maintained at 30° C. or less, then stirring was continued at 30° C. for 3 hours. While the solution obtained above was maintained at 10° C. or lower, 55.1 parts of 6-maleimidohexanoic acid chloride was added dropwise over 10 minutes, and then stirring was continued for 1 hour. 1 L of water was added to the solution obtained above, and the precipitate was collected and washed three times with pure water, and then dried in an oven at 60° C. for 2 days to obtain a bismaleimide compound (AP-2) of the present invention. A weight average molecular weight of the compound (AP-2) was 3,700.

Example 3

Synthesis of Bismaleimide Compound of the Present Invention 400 parts of N-methylpyrrolidone was charged into a 2-liter flask equipped with a stirrer and a thermometer, and 80.6 parts of 2,2'-bis(3-amino-4-hydroxyphenyl)hexafluoropropane and 61.3 parts of 2-methylpyridine were added and stirred and dissolved, and 35.9 parts of sebacic acid dichloride and 14.8 parts of 4,4'-dicarboxydiphenyl ether dichloride were added dropwise over 15 minutes while the solution was maintained at 30° C. or less, then stirring was continued at 30° C. for 3 hours. While the solution obtained above was maintained at 10° C. or lower, 22.0 parts of 6-maleimidohexanoic acid chloride was added dropwise over 10 minutes, and then stirring was continued for 1 hour. 1 L of water was added to the solution obtained above, and the precipitate was collected and washed three times with pure water, and then dried in an oven at 60° C. for 2 days to obtain a bismaleimide compound (AP-3) of the present invention. A weight average molecular weight of the compound (AP-3) was 10,900.

Example 4

Synthesis of Bismaleimide Compound of the Present Invention 400 parts of N-methylpyrrolidone was charged into a 2-liter flask equipped with a stirrer and a thermometer, and 80.6 parts of 2,2'-bis(3-amino-4-hydroxyphenyl)hexafluoropropane and 61.3 parts of 2-methylpyridine were added and stirred and dissolved, and 23.9 parts of sebacic acid dichloride and 29.5 parts of 4,4'-dicarboxydiphenyl ether dichloride were added dropwise over 15 minutes while the solution was maintained at 30° C. or less, then stirring was continued at 30° C. for 3 hours. While the solution obtained above was maintained at 10° C. or lower, 22.0 parts of 6-maleimidohexanoic acid chloride was added dropwise over 10 minutes, and then stirring was continued for 1 hour. 1 L of water was added to the solution obtained above, and the precipitate was collected and washed three times with pure water, and then dried in an oven at 60° C. for 2 days to obtain a bismaleimide compound (AP-4) of the present invention. A weight average molecular weight (Mw) of the compound (AP-4) was 10,500.

Example 5

Synthesis of Bismaleimide Compound of the Present Invention 100 parts of N-methylpyrrolidone was charged into a 1-liter flask equipped with a stirrer and a thermometer, and 29.3 parts of 2,2'-bis(3-amino-4-hydroxyphenyl)hexafluoropropane and 2,6 parts of 2-methylpyridine were added and stirred and dissolved, and 7.3 parts of adipic acid dichloride was added dropwise over 15 minutes while the solution was maintained at 30° C. or less, then stirring was continued at 30° C. for 3 hours. While the solution obtained above was maintained at 10° C. or lower, 22.0 parts of 6-maleimidohexanoic acid chloride was added dropwise over 10 minutes, and then stirring was continued for 1 hour. 0.5 L of water was added to the solution obtained above, and the precipitate was collected and washed three times with pure water, and then dried in an oven at 60° C. for 2 days to obtain a bismaleimide compound (AP-5) of the present invention. A weight average molecular weight (Mw) of the compound (AP-5) was 4,300.

Example 6

Synthesis of Bismaleimide Compound of the Present Invention 100 parts of N-methylpyrrolidone was charged into a 1-liter flask equipped with a stirrer and a thermometer, and 14.7 parts of 2,2'-bis(3-amino-4-hydroxyphenyl)hexafluoropropane and 13.2 parts of 2-methylpyridine were added and stirred and dissolved, and 3.7 parts of adipic acid dichloride was added dropwise over 15 minutes while the solution was maintained at 30° C. or less, then stirring was continued at 30° C. for 3 hours. While the solution obtained above was maintained at 10° C. or lower, 12.3 parts of 4(N-maleimidomethyl)cyclohexane-1-carboxylic acid chloride was added dropwise over 10 minutes, and then stirring was continued for 1 hour, 0.5 L of water was added to the solution obtained above, and the precipitate was collected and washed three times with pure water, and then dried in an oven at 60° C. for 2 days to obtain a bismaleimide compound (AP-6) of the present invention. A weight average molecular weight (Mw) of the compound (AP-6) was 4,500.

Example 7

Synthesis of Bismaleimide Compound of the Present Invention 100 parts of N-methylpyrrolidone was charged into a 1-liter flask equipped with a stirrer and a thermometer, and 12.1 parts of 2,2'-bis(3-amino-4-hydroxyphenyl)hexafluoropropane and 7.8 parts of 2-methylpyridine were added and stirred and dissolved, and 7.2 parts of sebacic acid dichloride was added dropwise over 15 minutes while the solution was maintained at 30° C. or less, then stirring was continued at 30° C. for 3 hours. While the solution obtained above was maintained at 10° C. or lower, 1.4 parts of 3-maleimidopropionic acid chloride was added dropwise over 10 minutes, and then stirring was continued for 1 hour. 0.5 L of water was added to the solution obtained above, and the precipitate was collected and washed three times with pure water, and then dried in an oven at 60° C. for 2 days to obtain a bismaleimide compound (AP-7) of the present invention. A weight average molecular weight (Mw) of the compound (AP-7) was 12,300.

Example 8

Synthesis of Bismaleimide Compound of the Present Invention 100 parts of N-methylpyrrolidone was charged into a 1-liter flask equipped with a stirrer and a thermometer, and 9.3 parts of bis(3-amino-4-hydroxyphenyl)sulfone and 7.8 parts of 2-methylpyridine were added and stirred and dissolved, and 7.2 parts of sebacic acid dichloride was added dropwise over 15 minutes while the solution was maintained at 30° C. or less, then stirring was continued at 30° C. for 3 hours. While the solution obtained above was maintained. at 10° C. or lower, 1.7 parts of 6-maleimidohexanoic acid chloride was added dropwise over 10 minutes, and then stirring was continued for 1 hour. 0.5 L of water was added to the solution obtained above, and the precipitate was collected and washed three times with pure water, and then dried in an oven at 60° C. for 2 days to obtain a bismaleimide compound (AP-8) of the present invention. A weight average molecular weight (Mw) of the compound (AP-8) was 10,700.

Comparative Example 1

Synthesis of Compound for Comparison 500 parts of N-methylpyrrolidone was charged into a 2-liter flask equipped with a stirrer and a thermometer, and 80.6 parts of 2,2'-bis(3-amino-4-hydroxyphenyl)hexafluoropropane and 52.3 parts of 2-inethylpyridine were added and stirred and dissolved, and 47.8 parts of sebacic acid dichloride was added dropwise over 15 minutes while the solution was maintained at 30° C. or less, then stirring was continued at 30° C. for 3 hours. 1 L of water was added to the solution obtained above, and the precipitate was collected and washed three times with pure water, and then dried in an oven at 60° C. for 2 days to obtain a bismaleimide compound for comparison (AC-1). A weight average molecular weight (Mw) of the compound (AC-1) was 10,000.

Comparative Example 2

Synthesis of Compound for Comparison 500 parts of N-methylpyrrolidone was charged into a 2-liter flask equipped with a stirrer and a thermometer, and 40.3 parts of 2,2'-bis(3-amino-4-hydroxyphenyl)hexafluoropropane and 24.7 parts of 2-methylpyridine were added and stirred and dissolved, and 20.3 parts of isophthalic acid dichloride was added dropwise over 15 minutes while the solution was maintained at 30° C. or less, then stirring was continued at 30° C. for 3 hours. While the solution obtained above was maintained at 10° C. or lower, 9.2 parts of 6-maleimidohexanoic acid chloride was added dropwise over 10 minutes, and then stirring was continued for 1 hour. 1 L of water was added to the solution obtained above, and the precipitate was collected and washed three times with pure water, and then dried in an oven at 60° C. for 2 days to obtain a bismaleimide compound for comparison (AC-2). A weight average molecular weight (Mw) of the compound (AC-2) was 38,300.

Comparative Example 3

Synthesis of Compound for Comparison

A compound for comparison (AC-3) represented by the following formula was synthesized using the method described in a patent literature U.S. Pat. No. 5,973,166. A weight average molecular weight (Mw) (in this case, equal to a "molecular weight") of the compound (AC-3) was 300.

C-3

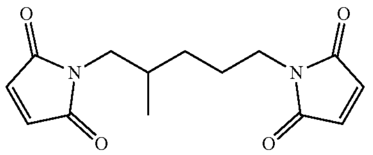

Examples 9 to 16 and Comparative Examples 4 to 6 (Preparation of Compositions of the Present Invention and for Comparison Components were blended in parts shown in Table 1 and Table 2 to prepare compositions of the present invention and for comparison.

Components used in compositions of Examples 9 to 16 and Comparative Examples 4 to 6 are as follows.

AP-1 to AP-8: bismaleimide compounds (AP-1) to (AP-8) obtained in Examples 1 to 8

AC-1 to AC-3: compounds (AC-1) to (AC-3) obtained in Comparative Examples 1 to 3

Photopolymerization initiator: ethanone, 1-[9-ethyl-6-(2-methylbenzoyl)-9H-carbazol-3-yl]-, 1-(O-acetyloxime) ("IRGACURE OXE-02" manufactured by BASF Japan Ltd.)

Solvent: N-methylpyrrolidone or cyclopentanone

Evaluation of Coating Properties of Composition

A silicon substrate was coated with each of the compositions obtained in Examples 9 to 16 and Comparative Examples 4 to 6 using a spin coater, and then appearance of the coat was visually confirmed to evaluate coating properties according to the following criteria. The results are shown in Tables 1 and 2.

o; A smooth film was obtained.

x; A smooth film was not obtained.

Evaluation of Alkali Developability of Composition

A silicon substrate was coated with each of the compositions obtained in Examples 9 to 16 and Comparative Examples 4 to 6 using a spin coater, and the coat was then dried at 95° C. for 15 minutes to form a composition layer having a thickness of 10 μm on the silicon substrate. The silicon substrate having the composition layer obtained above was immersed in 100 parts of a 2.38% tetramethylammonium hydroxide aqueous solution ("Tokusoh SD-1" manufactured by Tokuyama Corporation) for 5 minutes, and then a surface of the composition layer was visually confirmed to evaluate solubility according to the following evaluation criteria. The results are shown in Tables 1 and 2.

o; The surface of the composition layer was dissolved.

x; The surface of the composition layer was not dissolved.

Example 17

Preparation of Polymer Film and Cured Film Containing Polybenzoxazole of the Present Invention A 18 μm-thick copper foil was coated with the composition obtained in Example 9 using an applicator, and the coat was then dried at 100° C. for 120 minutes to form a 20 μm-thick composition layer on the copper foil. Using a conveyor UV irradiation device "CS30L-1-1" manufactured by GS Yuasa Corporation, the composition layer on the copper foil obtained above was exposed so that an exposure amount at a wavelength of 365 nm was 1000 mJ/$cm^2$, and then heated at 150° C. for 60 minutes to form a polymer film on the copper foil. The copper foil having the polymer film obtained above was heated at 225° C. for 120 minutes to perform an intramolecular dehydration ring-closing reaction of the polymer. Thereafter, the copper foil was removed by etching to obtain a cured film containing a polybenzoxazole of the present invention.

Examples 18 to 24 and Comparative Examples 7 to 9

Preparation of Polymer Film and Cured Film Containing Polybenzoxazole of the Present Invention, and Cured Film for Comparison Each of polymer films and cured films containing a polybenzoxazole of the present invention and cured films for comparison was produced by the same method as in Example 17 except that the composition obtained in Example 9 was changed to the compositions obtained in Examples 10 to 16 and Comparative Examples 4 to 6. However, as described in Table 2, in Comparative Example 7, a cured film was not obtained from the composition of Comparative Example 4.

Evaluation of Dielectric Properties (Dielectric Constant: Dk, Dielectric Dissipation Factor: Df) of Cured Film A plurality of cured films obtained in each of Examples 17 to 24 and Comparative Examples 8 to 9 cut into a length of 60 mm and a width of 3 mm were laminated, and then dried in a desiccator tilled with silica gel for 12 hours to prepare test pieces each having a film thickness of 50 to 300 μm. Using a vector type network analyzer "ADMSO10c1" manufactured by AET, Inc. as a measuring instrument and "CP531" (10 GHz band resonator) manufactured by Kanto Electronics Application & Development, Inc. as a cavity resonator, dielectric properties (dielectric constant: Dk, dielectric dissipation factor: Df) of each of the test pieces obtained above were measured by a cavity resonator perturbation method. The measurement conditions were a frequency of 10 GHz and a temperature of 25° C. The results are shown in Tables 1 and 2.

Evaluation of 5% Weight Loss Temperature of Cured Film

A weight loss temperature of each of the cured films obtained in Examples 17 to 24 and Comparative Examples 8 to 9 was measured under a temperature-rising condition of 10° C./min in nitrogen using a differential thermogravimeter ("TG/DTA 6200" manufactured by Seiko Instruments Inc.) to determine a 5% weight loss temperature. The results are shown in Tables 1 and 2.

TABLE 1

Components of compositions and evaluation results of polybenzoxazole films of Examples Components and properties of compositions

| | | Example | | | | | | | |
|---|---|---|---|---|---|---|---|---|---|
| Component | Material | 9 | 10 | 11 | 12 | 13 | 14 | 15 | 16 |
| Bismaleimide compound | AP-1 (Mw = 12,300) | 100 | | | | | | | |
| | AP-2 (Mw = 3,700) | | 100 | | | | | | |
| | AP-3 (Mw = 10,900) | | | 100 | | | | | |
| | AP-4 (Mw = 10,500) | | | | 100 | | | | |
| | AP-5 (Mw = 4,300) | | | | | 100 | | | |
| | AP-6 (Mw = 4,500) | | | | | | 100 | | |
| | AP-7 (Mw = 12,300) | | | | | | | 100 | |
| | AP-8 (Mw = 10,700) | | | | | | | | 100 |
| Photo-polymerization initiator | Irgacure OXE02 | 5 | 5 | 5 | 5 | 5 | 5 | 5 | 5 |
| Solvent | Cyclopentanone | 160 | 160 | 160 | 160 | 160 | 160 | 160 | 160 |
| Coating properties | Surface smoothness | ○ | ○ | ○ | ○ | ○ | ○ | ○ | ○ |
| Developability | Alkali solubility | ○ | ○ | ○ | ○ | ○ | ○ | ○ | ○ |

TABLE 1-continued

Components of compositions and evaluation results of polybenzoxazole films of Examples Properties of polybenzoxazole films

| Evaluation item | | Example 17 | 18 | 19 | 20 | 21 | 22 | 23 | 24 |
|---|---|---|---|---|---|---|---|---|---|
| Dielectric properties | Dk | 2.4 | 2.5 | 2.7 | 2.7 | 2.5 | 2.6 | 2.4 | 2.4 |
| | Df | 0.0041 | 0.0034 | 0.0042 | 0.0054 | 0.0050 | 0.0076 | 0.0037 | 0.0060 |
| Thermal properties | 5% Weight loss temperature | 300° C.< | 300° C.< | 300° C.< | 300° C.< | 300° C.< | 300° C.< | 300° C.< | 300° C.< |

TABLE 2

Components of compositions and evaluation results of cured films of Comparative Examples Components and properties of compositions

| Component | Material | Comparative Example 4 | 5 | 6 |
|---|---|---|---|---|
| Compound for comparison | AC-1 (Mw = 10,000) | 100 | | |
| | AC-2 (Mw = 38,300) | | 100 | |
| | AC-3 (Mw = 300) | | | 100 |
| Photopolymerization initiator | Irgacure OXE02 | 5 | 5 | 5 |
| Solvent | N-methylpyrrolidone | 160 | | 160 |
| | Cyclopentanone | | 160 | |
| Coating properties | Surface smoothness | ○ | ○ | X |
| Developability | Alkali solubility | *1 | ○ | X |
| Properties of cured films | | | | |

Properties of cured films

| Evaluated film | | Comparative Example 7 | 8 | 9 |
|---|---|---|---|---|
| Dielectric properties | Dk | *1 | 2.8 | 2.8 |
| | Df | *1 | 0.0111 | 0.0030 |
| Thermal properties | 5% Weight loss temperature | *1 | 300° C.< | 300° C.< |

The reference mark "*1" indicates that any composition layer or cured film was not obtained.

According to the results of Tables 1 and 2, the compositions of Examples 9 to 16 had good coating properties and solubility (developability), and the cured films containing a polybenzoxazole of Examples 17 to 24 obtained using these compositions exhibited excellent dielectric properties and thermal properties in spite of being formed under a heating condition at a lower temperature of 225° C.

On the other hand, a cured film could not be obtained from the composition of Comparative Example 4, and the cured film of Comparative Example 8 obtained using the composition of Comparative Example 5 had noticeably high Df. Furthermore, the composition of Comparative Example 6 had insufficient coating properties, and the composition layer obtained using the composition did not exhibit alkali solubility.

The polymer having the structural unit represented by formula (2) of the present invention is a photosensitive polybenzoxazole precursor having negative pattern-forming ability, and it is possible to use an alkaline aqueous solution for pattern formation. Therefore, it is possible to completely eliminate industrial waste of organic solvents which had been generated in a large amount so far. In addition, the polybenzoxazole film finally obtained is excellent in heat resistance and electrical properties in spite of being formed under a heating condition at a lower temperature of 225° C. Therefore, this cured film can be used as a surface protective film, an interlayer insulating film, and an insulating film of a rewiring layer of a semiconductor that is usually used. The present invention relates to a resin backbone itself used in a photosensitive resin composition and a method for producing the same. These are based on the invention that is perfectly novel, and it can be easily understood that this invention is unique and extremely excellent.

Other modifications and variations will be apparent to those skilled in the art in view of the above detailed description of the present invention. However, it is clear that such other modifications and variations may be practiced without departing from the spirit and scope of the present invention.

The invention claimed is:

1. A composition comprising: a bismaleimide compound represented by the following formula (1):

(1)

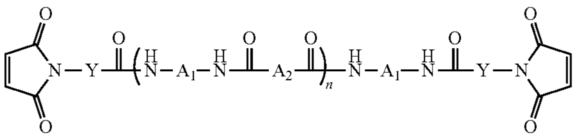

wherein, in formula (1), Ais each independently represent a direct bond, a divalent linking group represented by the following formula (1-1), (1-2), or (1-3):

(1-1)

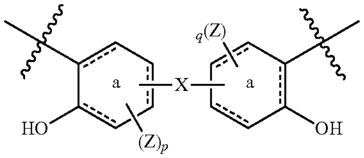

(1-2)

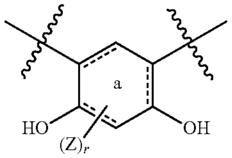

(1-3)

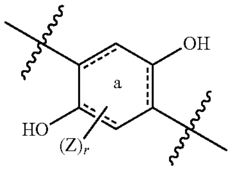

wherein, in formulas (1-1), (1-2), and (1-3), ring a represents a benzene ring or a cyclohexane ring; X represents a direct bond or a divalent linking group, and when a plurality of Xs is present in formula (1), the plurality of Xs may be the same as or different from each other; Z represents a monovalent substituent bonded to ring a, and when a plurality of Zs is present in formula (1), the plurality of Zs may be the same as or different from each other; p, q, and r are the number of monovalent substituents Z, p and q each independently represent an integer of 0 to 3, r represents an integer of 0 to 2, and when a plurality of ps is present in formula (1), the plurality of ps may be the same as or different from each other, when a plurality of qs is present in formula (1), the plurality of qs may be the same as or different from each other, and when a plurality of rs is present in formula (1), the plurality of rs may be the same as or different from each other;

or a divalent linking group other than formulas (1-1), (1-2), and (1-3) provided that at least one of the plurality of AS is a divalent linking group represented by formula (1-1), wherein Xs are each independently a divalent linking group represented by any one of the following formulas (a) to (e):

(a)

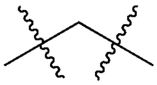

(b)

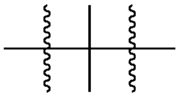

(c)

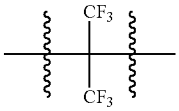

-continued (d)

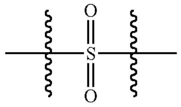

(e)

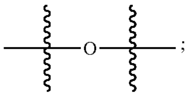

$A_2$ represents a divalent linking group obtained by removing two carboxy groups from a saturated aliphatic dicarboxylic acid compound, a divalent linking group obtained by removing two carboxy groups from an aromatic dicarboxylic acid compound, or a divalent linking group other than a divalent linking group obtained by removing two carboxy groups from a saturated aliphatic dicarboxylic acid compound and a divalent linking group obtained by removing two carboxy groups from an aromatic dicarboxylic acid compound, and when a plurality of $A_2$s is present, the plurality of $A_2$s may be the same as or different from each other; when $A_2$ is present singly, A2 is a divalent linking group obtained by removing two carboxy groups from a saturated aliphatic dicarboxylic acid compound, and when a plurality of A2s is present, at least one of the plurality of A2s is a divalent linking group obtained by removing two carboxy groups from a saturated aliphatic dicarboxylic acid compound; Y represents a divalent linking group, and a plurality of Ys may be the same as or different from each other; and n is an average value of the number of repeating units and is a real number in a range of 1 to 100; and a photopolymerization initiator or a curing catalyst.

2. The composition according to claim 1, wherein all of $A_1$s are a divalent linking group represented by formula (1-1), (1-2), or (1-3).

3. The composition according to claim 1, wherein at least one of $A_2$s is an alkylene group having 1 to 30 carbon atoms.

4. The composition according to claim 1, wherein all of $A_2$s are an alkylene group having 1 to 30 carbon atoms.

5. The composition according to claim 1, wherein at least one of $A_2$s is independently a divalent linking group obtained by removing two carboxy groups from a dicarboxylic acid compound selected from the group consisting of phthalic acid, isophthalic acid, 1, 4-benzenedicarboxylic acid, 4, 4'-dicarboxydiphenyl ether, 4, 4'-dicarboxydiphenyl sulfone, 4, 4'-biphenyldicarboxylic acid, benzophenone-4, 4'-dicarboxylic acid, and 4, 4'-stilbenedicarboxylic acid.

6. The composition according to claim 1, wherein Ys are each independently an alkylene group having 1 to 11 carbon atoms, or a divalent group containing a divalent aromatic group obtained by removing two hydrogen atoms from an aromatic ring of an aromatic hydrocarbon compound and an alkylene group having 1 to 11 carbon atoms.

7. A dry film resist comprising: two substrates; and the composition according to claim 1 sandwiched between the two substrates.

8. A polymer having 2 to 150 structural units represented by the following formula (2):

(2)

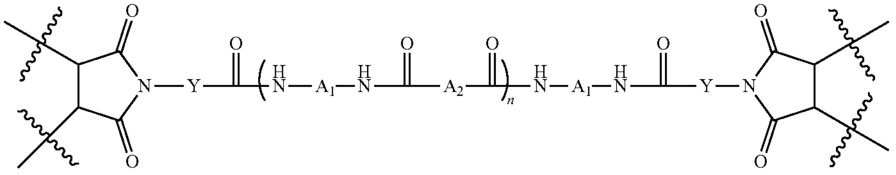

wherein $A_1$, $A_2$, Y, and n represent the same meaning as $A_1$, $A_{b\,2}$, Y, and n in formula (1), the polymer being a cured product of the composition according to claim 1.

9. A polybenzoxazole that is an intramolecular dehydrated ring-closed product of the polymer according to claim 8.

10. A semiconductor device comprising a surface protective film, an interlayer insulating film, or an insulating film of a rewiring layer, wherein the film contains the polybenzoxazole according to claim 9.

11. A polymer having 2 to 150 structural units represented by the following formula (2):

-continued (1-3)

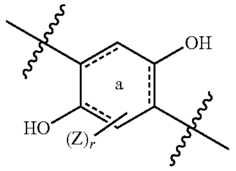

wherein, in formulas (1-1), (1-2), and (1-3), ring a represents a benzene ring or a cyclohexane ring; X repre- (2)

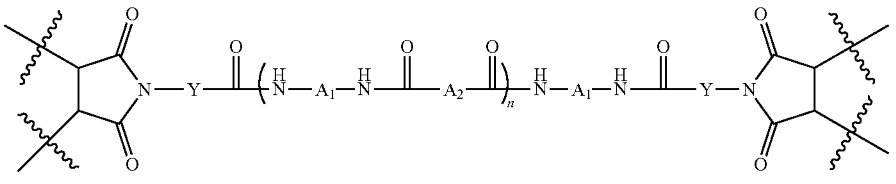

wherein $A_1$, $A_2$, Y, and n represent the same meaning as $A_1$, $A_2$, Y, and n in formula (1), the polymer being a self-polymer of a bismaleimide compound represented by the following formula (1):

(1)

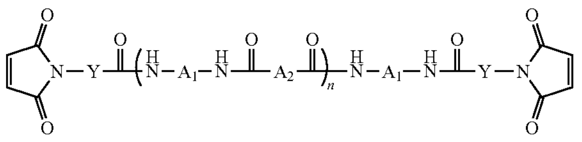

wherein, in formula (1), Ais each independently represent a direct bond, a divalent linking group represented by the following formula (1-1), (1-2), or (1-3):

(1-1)

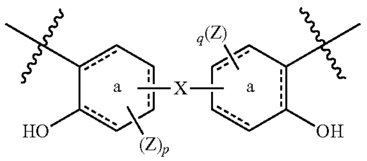

(1-2)

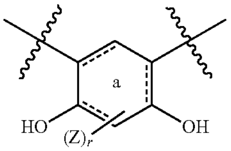

sents a direct bond or a divalent linking group, and when a plurality of Xs is present in formula (1), the plurality of Xs may be the same as or different from each other; Z represents a monovalent substituent bonded to ring a, and when a plurality of Zs is present in formula (1), the plurality of Zs may be the same as or different from each other; p, q, and r are the number of monovalent substituents Z, p and q each independently represent an integer of 0 to 3, r represents an integer of 0 to 2, and when a plurality of ps is present in formula (1), the plurality of ps may be the same as or different from each other, when a plurality of qs is present in formula (1), the plurality of qs may be the same as or different from each other, and when a plurality of rs is present in formula (1), the plurality of rs may be the same as or different from each other;

or a divalent linking group other than formulas (1-1), (1-2), and (1-3) provided that at least one of the plurality of Ais is a divalent linking group represented by formula (1-1), wherein Xs are each independently a divalent linking group represented by any one of the following formulas (a) to (e):

(a)

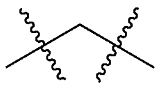

(b)

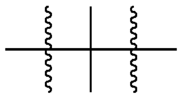

$A_2$ represents a divalent linking group obtained by removing two carboxy groups from a saturated aliphatic dicarboxylic acid compound, a divalent linking group obtained by removing two carboxy groups from an aromatic dicarboxylic acid compound, or a divalent linking group other than a divalent linking group obtained by removing two carboxy groups from a saturated aliphatic dicarboxylic acid compound and a divalent linking group obtained by removing two carboxy groups from an aromatic dicarboxylic acid compound, and when a plurality of A2s is present, the plurality of $A_2$s may be the same as or different from each other; when $A_2$ is present singly, A2 is a divalent linking group obtained by removing two carboxy groups from a saturated aliphatic dicarboxylic acid compound, and when a plurality of $A_2$s is present, at least one of the plurality of $A_2$S is a divalent linking group obtained by removing two carboxy groups from a saturated aliphatic dicarboxylic acid compound; Y represents a divalent linking group, and a plurality of Ys may be the same as or different from each other; and n is an average value of the number of repeating units and is a real number in a range of 1 to 100.

12. A polybenzoxazole that is an intramolecular dehydrated ring-closed product of the polymer according to claim 11.

13. A semiconductor device comprising a surface protective film, an interlayer insulating film, or an insulating film of a rewiring layer, wherein the film contains the polybenzoxazole according to claim 12.

14. A polymer having 2 to 150 structural units represented by the following formula (2):

(2)

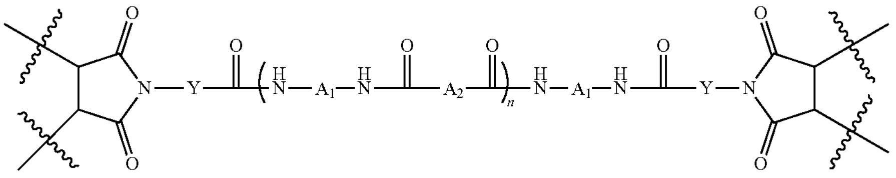

wherein $A_1$, $A_2$, Y, and n represent the same meaning as $A_1$, $A_2$, Y, and n in formula (1), the polymer being a copolymer of a composition comprising: a bismaleimide compound represented by the following formula (1):

(1)

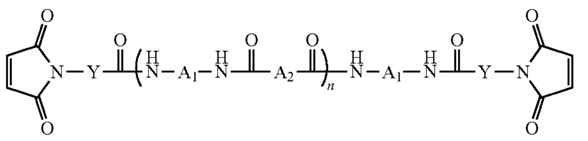

wherein, in formula (1), Ais each independently represent a direct bond, a divalent linking group represented by the following formula (1-1), (1-2), or (1-3):

(1-1)

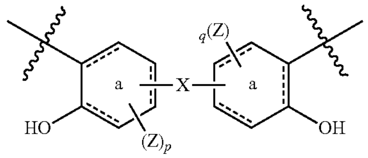

(1-2)

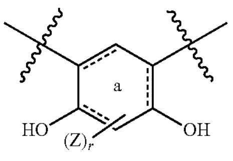

(1-3)

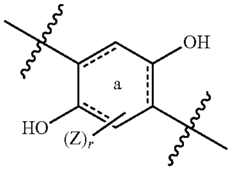

wherein, in formulas (1-1), (1-2), and (1-3), ring a represents a benzene ring or a cyclohexane ring; X represents a direct bond or a divalent linking group, and when a plurality of Xs is present in formula (1), the plurality of Xs may be the same as or different from each other; Z represents a monovalent substituent bonded to ring a, and when a plurality of Zs is present in formula (1), the plurality of Zs may be the same as or different from each other; p, q, and r are the number of monovalent substituents Z, p and q each independently represent an integer of 0 to 3, r represents an integer of 0 to 2, and when a plurality of ps is present in formula (1), the plurality of ps may be the same as or different from each other, when a plurality of qs is present in formula (1), the plurality of qs may be the same as or different from each other, and when a plurality of rs is present in formula (1), the plurality of rs may be the same as or different from each other;

or a divalent linking group other than formulas (1-1), (1-2), and (1-3) provided that at least one of the plurality of $A_1$s is a divalent linking group represented by formula (1-1), wherein Xs are each independently a divalent linking group represented by any one of the following formulas (a) to (e):

(a)

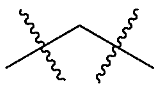

-continued (b)

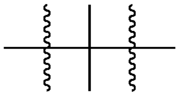

(c)

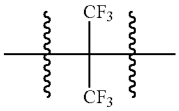

(d)

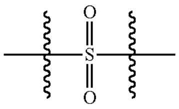

(e)

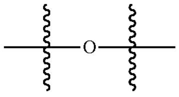

;

$A_2$ represents a divalent linking group obtained by removing two carboxy groups from a saturated aliphatic dicarboxylic acid compound, a divalent linking group obtained by removing two carboxy groups from an aromatic dicarboxylic acid compound, or a divalent linking group other than a divalent linking group obtained by removing two carboxy groups from a saturated aliphatic dicarboxylic acid compound and a divalent linking group obtained by removing two carboxy groups from an aromatic dicarboxylic acid compound, and when a plurality of $A_2$s is present, the plurality of $A_2$s may be the same as or different from each other; when $A_2$ is present singly, $A_2$ is a divalent linking group obtained by removing two carboxy groups from a saturated aliphatic dicarboxylic acid compound, and when a plurality of A2s is present, at least one of the plurality of A2S is a divalent linking group obtained by removing two carboxy groups from a saturated aliphatic dicarboxylic acid compound; Y represents a divalent linking group, and a plurality of Ys may be the same as or different from each other; and n is an average value of the number of repeating units and is a real number in a range of 1 to 100; and a compound capable of reacting with a maleimide group.

15. A polybenzoxazole that is an intramolecular dehydrated ring-closed product of the polymer according to claim 14.

16. A semiconductor device comprising a surface protective film, an interlayer insulating film, or an insulating film of a rewiring layer, wherein the film contains the polybenzoxazole according to claim 15.

17. A bismaleimide compound represented by the following formula (1):

(1)

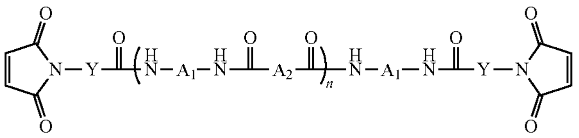

wherein, in formula (1), Ais each independently represent a direct bond, a divalent linking group represented by the following formula (1-1), (1-2), or (1-3):

(1-1)

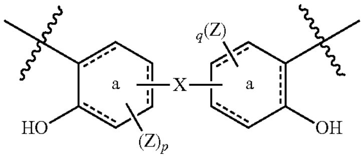

(1-2)

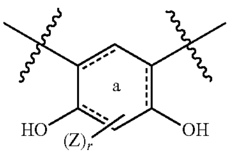

(1-3)

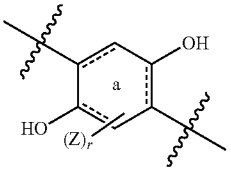

wherein, in formulas (1-1), (1-2), and (1-3), ring a represents a benzene ring or a cyclohexane ring; X represents a direct bond or a divalent linking group, and when a plurality of Xs is present in formula (1), the plurality of Xs may be the same as or different from each other; Z represents a monovalent substituent bonded to ring a, and when a plurality of Zs is present in formula (1), the plurality of Zs may be the same as or different from each other; p, q, and r are the number of monovalent substituents Z, p and q each independently represent an integer of 0 to 3, r represents an integer of 0 to 2, and when a plurality of ps is present in formula (1), the plurality of ps may be the same as or different from each other, when a plurality of qs is present in formula (1), the plurality of qs may be the same as or different from each other, and when a plurality of rs is present in formula (1), the plurality of rs may be the same as or different from each other;

or a divalent linking group other than formulas (1-1), (1-2), and (1-3) provided that at least one of the plurality of $A_1$s is a divalent linking group represented by formula (1-1), wherein Xs are each independently a divalent linking group represented by any one of the following formulas (a) to (e):

(a)

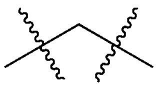

(b)

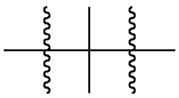

(c)

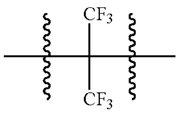

(d)

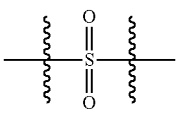

-continued (e)

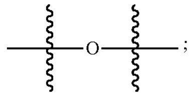

$A_2$ represents a divalent linking group obtained by removing two carboxy groups from a saturated aliphatic dicarboxylic acid compound, a divalent linking group obtained by removing two carboxy groups from an aromatic dicarboxylic acid compound, or a divalent linking group other than a divalent linking group obtained by removing two carboxy groups from a saturated aliphatic dicarboxylic acid compound and a divalent linking group obtained by removing two carboxy groups from an aromatic dicarboxylic acid compound, and when a plurality of $A_2$s is present, the plurality of $A_2$s may be the same as or different from each other; when $A_2$ is present singly, $A_2$ is a divalent linking group obtained by removing two carboxy groups from a saturated aliphatic dicarboxylic acid compound, and when a plurality of $A_2$s is present, at least one of the plurality of $A_2$S is a divalent linking group obtained by removing two carboxy groups from a saturated aliphatic dicarboxylic acid compound; Y represents a divalent linking group, and a plurality of Ys may be the same as or different from each other; and n is an average value of the number of repeating units and is a real number in a range of 1 to 100, and wherein at least one of $A_2$s is independently a divalent linking group obtained by removing two carboxy groups from a dicarboxylic acid compound selected from the group consisting of phthalic acid, isophthalic acid, 1, 4-benzenedicarboxylic acid, 4, 4'-dicarboxydiphenyl ether, 4, 4'-dicarboxydiphenyl sulfone, 4, 4'-biphenyldicarboxylic acid, benzophenone-4, 4'-dicarboxylic acid, and 4, 4'-stilbenedicarboxylic acid.

* * * * *